(12) United States Patent
Ingber et al.

(10) Patent No.: US 8,519,358 B2
(45) Date of Patent: Aug. 27, 2013

(54) SYSTEM FOR CONDUCTING THE IDENTIFICATION OF BACTERIA IN BIOLOGICAL SAMPLES

(75) Inventors: Gal Ingber, Oranit (IL); William G. Atterbury, Columbus, OH (US); Dave Holley, Lancaster, OH (US); John S. Laudo, Columbus, OH (US); Jason A. Schaefer, Plainfield, IN (US); Sherwood Talbert, Columbus, OH (US); John Tallarico, Powell, OH (US); Thomas A. Klausing, Powell, OH (US)

(73) Assignee: Pocared Diagnostics Ltd. (IL)

( * ) Notice: Subject to any disclaimer, the term of this patent is extended or adjusted under 35 U.S.C. 154(b) by 156 days.

(21) Appl. No.: 12/865,186

(22) PCT Filed: Feb. 5, 2009

(86) PCT No.: PCT/US2009/033186
§ 371 (c)(1),
(2), (4) Date: Oct. 26, 2010

(87) PCT Pub. No.: WO2009/100197
PCT Pub. Date: Aug. 13, 2009

(65) Prior Publication Data
US 2011/0042582 A1 Feb. 24, 2011

Related U.S. Application Data

(60) Provisional application No. 61/026,300, filed on Feb. 5, 2008, provisional application No. 61/026,309, filed on Feb. 5, 2008, provisional application No. 61/026,324, filed on Feb. 5, 2008, provisional application No. 61/026,336, filed on Feb. 5, 2008, provisional application No. 61/026,357, filed on Feb. 5, 2008, provisional application No. 61/026,374, filed on Feb. 5, 2008.

(51) Int. Cl.
*G01J 1/58* (2006.01)
(52) U.S. Cl.
USPC ............................ 250/458.1; 356/246
(58) Field of Classification Search
USPC ............................................ 250/458.1
See application file for complete search history.

(56) References Cited

U.S. PATENT DOCUMENTS 4,360,360 A 11/1982 Chiknas
4,406,547 A 9/1983 Aihara
(Continued)

FOREIGN PATENT DOCUMENTS

GB 2019563 A 10/1979
JP 04-348250 A 12/1992
(Continued)

OTHER PUBLICATIONS

Giana et al., Rapid Identification of Bacterial Species by Fluorescence Spectroscopy and Classification Through Principal Components Analysis, Journal of Fluorescence, Nov. 2003, pp. 489-493, vol. 13, No. 6.

*Primary Examiner* — Marcus Taningco
(74) *Attorney, Agent, or Firm* — The Webb Law Firm

(57) ABSTRACT

The present invention relates to a system for conducting the identification and quantification of micro-organisms, e.g., bacteria in biological samples. More particularly, the invention relates to a system comprising a disposable cartridge and an optical cup or cuvette having a tapered surface; an optics system including an optical reader and a thermal controller; an optical analyzer; a cooling system; and an improved spectrometer. The system may utilize the disposable cartridge in the sample processor and the optical cup or cuvette in the optical analyzer.

32 Claims, 32 Drawing Sheets

(56) References Cited

U.S. PATENT DOCUMENTS

| | | |
|---|---|---|
| 4,477,186 A | 10/1984 | Carlson |
| 4,509,856 A | 4/1985 | Lee |
| 4,556,636 A | 12/1985 | Belly et al. |
| 4,873,993 A | 10/1989 | Meserol et al. |
| 4,918,984 A * | 4/1990 | Martinoli et al. ............ 73/64.43 |
| 5,314,825 A | 5/1994 | Weyrauch et al. |
| 5,578,269 A | 11/1996 | Yaremko et al. |
| 5,605,665 A | 2/1997 | Clark et al. |
| 5,700,428 A * | 12/1997 | Carlson ....................... 422/82.08 |
| 5,797,147 A * | 8/1998 | Young et al. ................... 4/144.1 |
| 6,515,745 B2 | 2/2003 | Vurens et al. |
| 6,559,941 B1 | 5/2003 | Hammer |
| 6,767,511 B1 * | 7/2004 | Rousseau ........................ 422/73 |
| 6,773,922 B2 | 8/2004 | Jeng et al. |
| 7,206,620 B2 | 4/2007 | Erickson et al. |
| 7,277,175 B2 | 10/2007 | Thompson et al. |
| 7,299,079 B2 | 11/2007 | Rebec et al. |
| 7,303,922 B2 | 12/2007 | Jeng et al. |
| 7,959,878 B2 * | 6/2011 | Rousseau ....................... 422/554 |
| 2005/0110980 A1 | 5/2005 | Maehara et al. |
| 2005/0110989 A1 | 5/2005 | Schermer |
| 2005/0175502 A1 * | 8/2005 | Rousseau et al. ................ 422/64 |
| 2005/0271550 A1 | 12/2005 | Talmer et al. |
| 2006/0013729 A1 | 1/2006 | Carey et al. |
| 2007/0037135 A1 | 2/2007 | Barnes et al. |
| 2007/0189925 A1 | 8/2007 | Blecka et al. |
| 2008/0003665 A1 * | 1/2008 | Potyrailo et al. ........... 435/287.2 |
| 2008/0297796 A1 | 12/2008 | Lukas et al. |
| 2008/0297798 A1 | 12/2008 | Wyssen |
| 2009/0067280 A1 | 3/2009 | Ammann et al. |
| 2010/0208256 A1 * | 8/2010 | Tang et al. .................... 356/326 |

FOREIGN PATENT DOCUMENTS

| | | |
|---|---|---|
| JP | 05-001989 A | 1/1993 |
| JP | 2006-349582 A | 12/2006 |
| WO | 2004055522 A1 | 7/2004 |
| WO | 2005124365 A2 | 12/2005 |
| WO | 2007039524 A2 | 4/2007 |
| WO | 2007085715 A1 | 8/2007 |
| WO | 2009/049171 A2 | 4/2009 |

* cited by examiner

SYSTEM FOR CONDUCTING THE IDENTIFICATION OF BACTERIA IN BIOLOGICAL SAMPLES

CROSS REFERENCE TO RELATED APPLICATIONS

The present application claims priority to U.S. Provisional Application Nos. 61/026,300; 61/026,309; 61/026,324; 61/026,336; 61/026,357; and 61/026,374, all filed on Feb. 5, 2008, which are herein incorporated by reference in their entirety.

BACKGROUND OF TIM INVENTION

1. Field of the Invention

The present invention relates to a system for conducting the identification and quantification of micro-organisms, e.g., bacteria in biological samples such as urine. More particularly, the invention relates to a system comprising a disposable cartridge and an optical cup or cuvette having a tapered surface; an optics system including an optical reader and a thermal controller; an optical analyzer and an improved spectrometer. The system may utilize the disposable cartridge in the sample processor and the optical cup or cuvette in the optical analyzer.

2. Description of Related Art

In general, current-day practice for identifying micro-organisms, e.g., bacteria in urine samples, involves a complex, lengthy, and expensive process for identifying and specifying micro-organisms in microbiology labs. In the current process, the samples are accepted into the lab. These specimens are then sorted, labeled, and then they are inoculated onto blood agar medium using a sterilized loop. The specimens are then inserted into a dedicated incubator for a 24-hour period. A day later, the lab technicians screen the specimens for positive and negative cultures. In general, most of the cultures are negative and they are manually reported. The organisms for the positive cultures are isolated and suspended in a biochemical fluid. This involves suspension, dilution, vortexing, and turbidity measurements resulting in biochemical waste products. The cultures are then subjected to a species identification and antibiotics susceptibility testing exposing the suspensions to multiple reagents. After another 6 to 24-hour incubation period, the findings are interpreted and reported by lab technicians. This entire process generally takes 11 steps and 50 hours to obtain specimen results and the process is labor intensive.

Commonly owned U.S. Publication No. US 2007/0037135 A1, the contents of which are herein incorporated by reference, discloses a system for identification and quantification of a biological sample suspended in a liquid. As disclosed in the reference sample cuvettes are used for holding the biological sample. The reference states that these cuvettes are said to be well known in the art, are typically square or rectangular in shape (having a well area to contain the sample), and are made of a transparent material such as glass or a polymeric material. However, the reference fails to disclose any specific description/design of the cuvettes.

There is a need, therefore, particularly for species identification of the above lab procedure to provide a more efficient and less time consuming process which requires less labor. There is also a need for an improved design for an optics cup or cuvette and a method for manufacturing the optics cup or cuvette or for holding samples, which optics cup or cuvette may be used in a system for an optical analysis of the sample.

SUMMARY OF THE INVENTION

The system of the invention streamlines the current system for obtaining specimen results. The system is environmentally friendly, enables a rapid diagnosis, results are consistent, no reagents are needed, and there is a multifunctional diagnosis. According to one embodiment disclosed in commonly owned PCT Application US2008/079533, biological samples are contained within disposable cartridges which hold four disposable components, i.e., a centrifuge, two pipette tips with a different volume, and an optical cuvette. The cartridges are bar coded and tied in with the patient's ID. The cartridges are inserted in a magazine which is then inserted into a sample processor which processes the specimens. The prepared specimens are transferred into the optical cuvettes and then the magazine is inserted into an optical analyzer which analyses the specimens. The optical analyzer analyses and generates the complete results enabling ultimate treatment of the bacteria. The system does not require a sophisticated operator and gives rapid results.

According to an alternative embodiment, the system includes a plurality of disposable cartridges for holding a plurality of disposable components including a centrifuge tube, a pipette tip having a 1 ml volume, and an optics cup or cuvette containing a biological specimen, such as urine, wherein the optics cup or cuvette is specifically shaped to optimize analysis of the contents. Each cartridge is bar coded and tied to a urine specimen of a patient. The centrifuge tube and the pipette tip may generally be used for processing or preparing the urine specimen for analysis and the final processed urine sample is then transferred into the optics cup or cuvette for optical analysis in an optical analyzer. The optics cup or cuvette includes a container that has a lower tapered area in order to assist with the optical analysis. That is, the ultraviolet (UV) light source used in the optical analysis can be directed into the optics cup or cuvette. The optics cup or cuvette may be made of a transparent material, for example ABS plastic or glass, or it may be made of a metallic material, e.g., aluminum. If the optics cup or cuvette is made of a transparent material, then, preferably, it is coated or layered with a reflective material. In particular, an inner surface of the optics cup or cuvette is coated with a reflective material or contains a layer of reflective material. One or more disposable cartridges may be inserted into a magazine, which can then be inserted into a sample processor and/or into an optical analyzer. As many as 42 urine samples may be processed and then optically analyzed while being supported in an optics cup or cuvette which, in turn, is supported in a disposable cartridge of the invention. The samples or specimens may be biological samples, chemical samples, or toxicant samples, including, for example, urine samples for the optical analysis of contaminants, e.g., bacteria.

In an additional embodiment, the present invention relates to an optics cup or cuvette referred to above for holding a sample, e.g. biological sample, chemical sample, or toxicant sample, e.g. urine for optical analysis. If the sample is a urine sample, then the optical analysis would be for micro-organism or organisms, e.g. bacteria in the urine. The optics cup or cuvette may be a rectangular-shaped container, and preferably an injection molded plastic having an upper rectangular opening and a tapered area extending inwardly and downwardly relative to the rectangular opening.

In an additional embodiment, the optical cup or cuvette includes a rectangular-shaped container having a lower tapered area, a rectangular-shaped top opening for receiving the biological fluid specimen, and an inner reflective surface. The container also includes two parallel spaced-apart sidewalls, two spaced-apart end walls and a horizontal floor. The two spaced-apart end walls have a first end wall with the lower tapered area which is contiguous to the horizontal floor. The horizontal floor has a width of about 7 mm and a length of about 16 mm. The sidewalls and the second end wall have a depth of about 18 mm, and the first end wall has a depth of about 11 mm. The lower tapered area has a length of about 7 mm and is angled about 45° relative to the first end wall.

In another aspect, the disposable optical cup or cuvette also has a flange along the perimeter of the rectangular-shaped opening at the top of the container for supporting the optical cup or cuvette, preferably, in a disposable cartridge during optical analysis of the biological fluid specimen and which optical analysis generally involves an optical reader.

According to another aspect of the invention, the optical reader for analyzing bacteria in the biological specimen includes the optics cup containing the biological specimen and an illumination arrangement including a xenon light source and a system of turning mirrors, filters and a filter wheel supported in a plurality of carriages for producing an illumination beam. The plurality of carriages are arranged at an angle so as to decrease the distance between the light source and the optics cup and to increase the signal-to-noise ratio of the illumination beam. The optical reader also includes an anchor shoe for supporting the optics cup and having a slit for producing a collimated beam from the illumination beam and directing the collimated beam into the optics cup and an optical collection device for receiving the fluorescent emissions of the collimated beam from the urine specimen and the optics cup and directing the fluorescent emissions to a detection device for the analysis of bacteria in the urine specimen.

According to another aspect of the invention, there is provided a method for increasing the signal-to-noise ratio of a collimated beam generated in an optical reader for the optical analysis of a biological specimen contained in an optics cup. The method comprises providing a light source for producing an illumination beam; directing the illumination beam into a first optical system including a filter and a turning mirror so as to bend the path of travel of the illumination beam of the light source; directing the illumination beam produced in step b) into a second optical system including a filter and a turning mirror so as to bend the path of travel of the illumination beam produced in step b) at a 45° angle; and directing the illumination beam as a result of step c) into a slit to produce a collimated beam which is directed into the urine specimen in the optics cup to produce fluorescent emissions which are directed to an optical collection device and then to a detection device for the analysis of bacteria in the urine specimen.

In an embodiment of the invention, the optical cup or cuvette includes a ribbon liner for light collection and reflection through the sample for the optical analysis of the sample. The ribbon liner may be made of a reflective material, for example, a piece of stamped aluminum, which may be shaped and formed to partially or totally clad the inner surface of the container including the tapered area. The ribbon liner may be secured to the container via a crimping process wherein the ends of the ribbon liner are fastened to the flanges of the rectangular opening of the container, or via a one-way retention tab, or via one or two heat staked pins, or via a snap mechanism which may be tooled out of the side of the container. These means for securing the wet ribbon liner to the inner surface of the container are well-known to those skilled in the art. For example, the one-way retention tab includes the container having a post which has small "teeth" and the liner having a hole or opening and once the liner is positioned over the post, the "teeth" of the post prevent the liner from being moved. A heat stake pin is generally smooth and once the liner is positioned on the pin, heat is used to deform the end so that the liner cannot slip out of the container.

In a further embodiment of the invention, the inner surface of the container is partially or totally coated with a layer of aluminum through a process selected from the group consisting of a vacuum metallization process and an electroplating process. In a further embodiment of the invention, the container may be a two-piece construction having an upper piece with a rectangular opening for receiving the urine sample and a lower piece having a tapered area for re-directing light. The upper and lower pieces are bonded together and the lower piece can contain a ribbon layer of a reflective material or a coating of reflective material, for example, aluminum. The bonding process may be selected from the group consisting of an ultrasonic butt welding process, an ultrasonic shear welding process, a press fit process, a snap fit process and a solvent weld process using a press fit process or a snap fit process.

The disposable cartridge of the invention for containing the disposable components including the optics cup or cuvette discussed above can be formed by an injection molding process from a well-known plastic material, such as an ABS plastic. The disposable cartridge contains several compartments for positioning and supporting the several disposable components such as the centrifuge tube, pipette and optics cup or cuvette discussed hereinabove. The compartments for positioning and supporting the centrifuge tube and pipette generally are cylindrical in shape so as to receive the cylindrical shapes of the centrifuge tube and pipette and better support these components within the disposable cartridge. However, the compartment for positioning and supporting the optics cup or cuvette, particularly if the optics cup or cuvette is rectangular-shaped, need not be molded in the same configuration as the optics cup or cuvette. In this instance, the compartment for the optics cup or cuvette in the disposable cartridge may, in general, include a rectangular-shaped opening located in the top surface of the disposable cartridge wherein a top flange of the optics cup or cuvette engages and is supported by the top surface of the disposable cartridge and the optics cup or cuvette is suspended within the disposable cartridge.

In one embodiment, the system includes a plurality of disposable cartridges for holding a plurality of disposable components including: a centrifuge tube; a pipette tip; and an optical urine sample cuvette; a sample processor for receiving the plurality of disposable cartridges and configured to process and prepare the urine sample of each disposable cartridge and to transfer the urine samples into the respective optical cuvette of each of the disposable cartridges; and an optical analyzer for receiving the cartridge with the optical cuvettes containing the processed urine samples and analyzing and generating the specimen results. The entire process of processing the urine specimens in the sample processor and analyzing them in the optical analyzer takes about 30 minutes for a single specimen and up to 2 hours for 42 specimens.

The disposable cartridge and the disposable components of the present invention provide advantages over the currently used cartridges and components as they increase efficiency, improve workload and save time and money since the components necessary for the preparation or processing of the urine samples are conveniently located in one place, i.e., in a cartridge. Additionally, less manpower or manual handling of the components is required for the processing/analyzing of the urine samples. There is also the added convenience in that the cartridge and its components are disposable. That is, these items do not need to be sterilized for the next urine specimen identification process and contamination of the work area and/or surrounding environment is minimized.

According to another aspect of the invention, there is provided a system for cooling and controlling the temperature of a sample, e.g. urine sample in an optics cup or cuvette for optical analysis and the system may be located in an optical analyzer which performs analysis of one or more samples.

In an additional embodiment, the system of the present invention includes: a carousel for supporting a plurality of disposable cartridges, each supporting a disposable optics cup or cuvette containing a sample or specimen to be optically analyzed by an optical analyzer and having a plurality of openings, each associated with one of the disposable cartridges; a turntable having a plurality of openings each associated with one of the openings in the carousel; a tubing system surrounding the turntable for carrying chilled air from a thermal electrical (TE) cooler to the turntable and cool air from the turntable to the TE cooler; and a fan associated with the tubing system for circulating chilled air through the plurality of openings in the turntable to cool and to control the temperature of the specimens. The turntable, preferably, is made of aluminum, and the optics cups or cuvettes and disposable cartridges are preferably made of plastic thereby enabling convective cooling to occur through the aluminum material and the plastic material for rapidly cooling the specimens and then maintaining the specimens at a desired temperature during the optical analysis of the specimens or samples.

In one embodiment, the system of the invention may be located in an optical analyzer and may be adapted to cool the specimens from ambient temperature down to a desired temperature, for example, about 18° C. within about 5 minutes after start up of the optical analyzer and then controlling the temperature of the samples to within ±0.5° C. of the desired temperature until the optical processing of the samples in the optical analyzer is completed. The openings in the turntable are about 0.156-inch holes and deliver an air flow rate ranging from about 15 to about 10 cubic feet per minute. The temperature of the chilled water traveling from the TE cooler to the turntable is maintained at ±0.1° C. of the cool down temperature, and the rate of flow of the cooling water traveling from the turntable to the TE cooler is about 0.5 to about 1.0 gallons per minute.

A further embodiment of the present invention provides a system for cooling and then controlling the temperature of a specimen in an optics cup or cuvette during optical analysis, including: a carousel for supporting a plurality of disposable cartridges which support a plurality of disposable optics cups or cuvettes, each containing a specimen to be optically analyzed by an optical analyzer, and having a plurality of openings, each associated with one of the disposable cartridges; a turntable having a plurality of openings, each associated with one of the openings in the carousel; and an aluminum block located below the turntable and having a plurality of passageways in association with the turntable for carrying chilled air from a TE cooler to the turntable and cool air from the turntable to the TE cooler for cooling the samples and then controlling the temperature of the specimens.

In one embodiment the present invention provides a system for cooling and controlling the temperature of the samples being subjected to an optical analysis so that the signal of the specimens may be maintained for an adequate analysis of the organisms in the specimens.

In yet another embodiment, the present invention provides an improved arrangement for a spectrometer for use in an optical reader for optically analyzing a specimen. The spectrometer includes a collection lens system for receiving an illumination beam from the optics cup or cuvette containing the specimen; a spectrometer slit arranged adjacent the collection lens system through which the illumination beam travels in a first optical path after exiting the optics cup or cuvette; a first cylindrical lens located adjacent the spectrometer slit for receiving the illumination beam in its first optical path; a first mirror for collimating the illumination beam traveling through the first cylindrical lens and for reflecting the illumination beam into a second optical path; a plane diffraction grating located in the second optical path of the illumination beam for receiving the illumination beam reflected from the first mirror, for dispersing the illumination beam into its spectral components to form a plurality of dispersed beams and for reflecting the dispersed beams along a third optical path; a second mirror in the third optical path; a second cylindrical lens positioned relative to the second mirror for receiving and focusing the plurality of dispersed beams toward the second cylindrical lens in a fourth optical path; and a CCD device allocated adjacent the second cylindrical lens for receiving the plurality of dispersed beams traveling through the second cylindrical lens for the analysis of the presence of contaminants, e.g. bacteria in the specimen, e.g. biological fluid, e.g., urine.

In one embodiment, the first and second cylindrical lenses are preferably 3-inch spherical mirrors having ultraviolet (UV) lenses made of fused silica material. The first cylindrical lens is preferably located about 10.7 mm from the spectrometer slit. The first mirror is located closer to the slit than the second mirror and the first mirror and the second mirror have a radius of about 360 m. The grating is preferably a 3-inch grating, preferably having 1200 lines per millimeter (lpm) and blazed 10.4° for a 300 nm wavelength region. The CCD includes a 25 mm length detector.

In one embodiment the present invention provides an improved spectrometer for the optical reading of bacteria in a urine specimen which increases the throughput in a spectrometer.

In a further embodiment, the present invention provides an improved arrangement for a spectrometer useful in a system which has low resolution and high sensitivity conditions.

In one aspect of the invention, the optical analyzer contains an optics system, a thermal control, and a drawer which has a rotatable table for receiving, supporting, and rotating a magazine containing a plurality of disposable cartridges with optical cups or cuvettes which contain the urine samples to be analyzed. The optical analyzer also contains a bar code reader for inventorying the urine samples. When the drawer with the magazine is inserted into the optical analyzer, the drive mechanism for the rotatable table supporting the magazine rotates and registers the magazine relative to the bar code reader and then rotates and registers the magazine relative to the optics system. The optics system includes an excitation module unit, an optical collection unit, and a spectrometer. The temperature of each cup or cuvette is decreased to a temperature which will slow the metabolism of the bacteria in the urine samples while increasing the fluorescence signal. A thermal control cools a large thermal mass, which is located on the rotatable table underneath the magazine containing the disposable cartridges, with urine sample cups or cuvettes.

In one embodiment, a related method for identifying the type of micro-organism and quantifying it in a urine sample includes the steps of obtaining a urine sample; passing the urine sample through a 10 micron filter; obtaining a 2 ml sample of the filtered urine and placing it into a centrifuge tube; obtaining a 1,000,000:1 dilution of the dissolved materials in the urine retaining bacteria in the urine sample by centrifuging the 2 ml sample at about a 12,000 g-force, decanting about 95% of the fluid in the centrifuge tube, replacing the decanted solution with a saline solution, and repeating these steps about five times; transferring the final solution into an optical cup or cuvette; and subjecting the optical cup or cuvette to an optical analysis having optics, which include exciting the urine sample with at least five different wavelengths, collecting and detecting the fluorescent emissions; and directing the fluorescent emissions into a spectrometer. The fluid sample may be for example a biological, chemical or toxicant sample, e.g., urine sample which is optically analyzed, for example, for the type and amount of organism or micro-organism, e.g., bacteria in the sample.

In an additional embodiment, the fluid sample may be for example a biological, chemical or toxicant sample, e.g., urine sample which is optically analyzed, for example, for the type and amount of organism or micro-organism, e.g., bacteria in the sample.

These and other objects and advantages of the invention will be made apparent from the following description taken together with the drawings.

DETAILED DESCRIPTION OF THE INVENTION

Figure 1A:
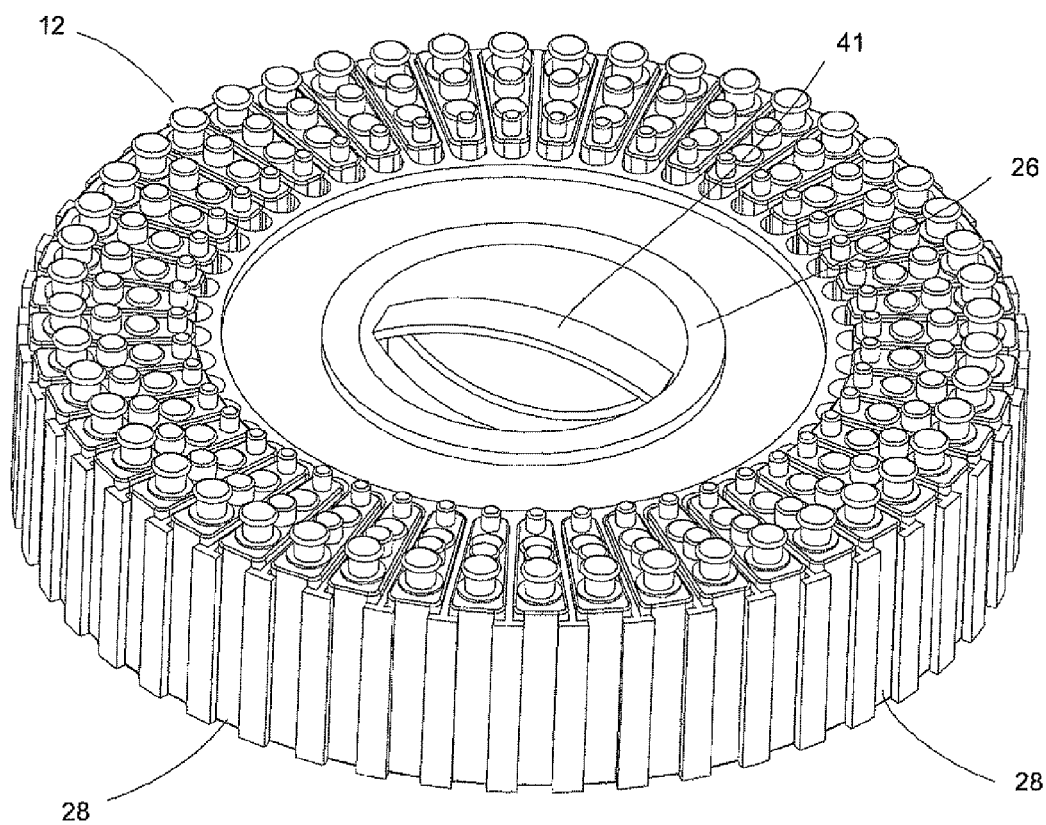
FIG. 1A is a top perspective view of a magazine having a plurality of disposable cartridges.

The present invention will be described with reference to the accompanying drawings where like reference numbers correspond to like elements.

For purposes of the description hereinafter, spatial or directional terms shall relate to the invention as it is oriented in the drawing figures. However, it is to be understood that the invention may assume various alternative variations, except where expressly specified to the contrary. It is also to be understood that the specific components illustrated in the attached drawings, and described in the following specification, are simply exemplary embodiments of the invention.

Hence, specific dimensions and other physical characteristics related to the embodiments disclosed herein are not to be considered as limiting.

Figure 1B:
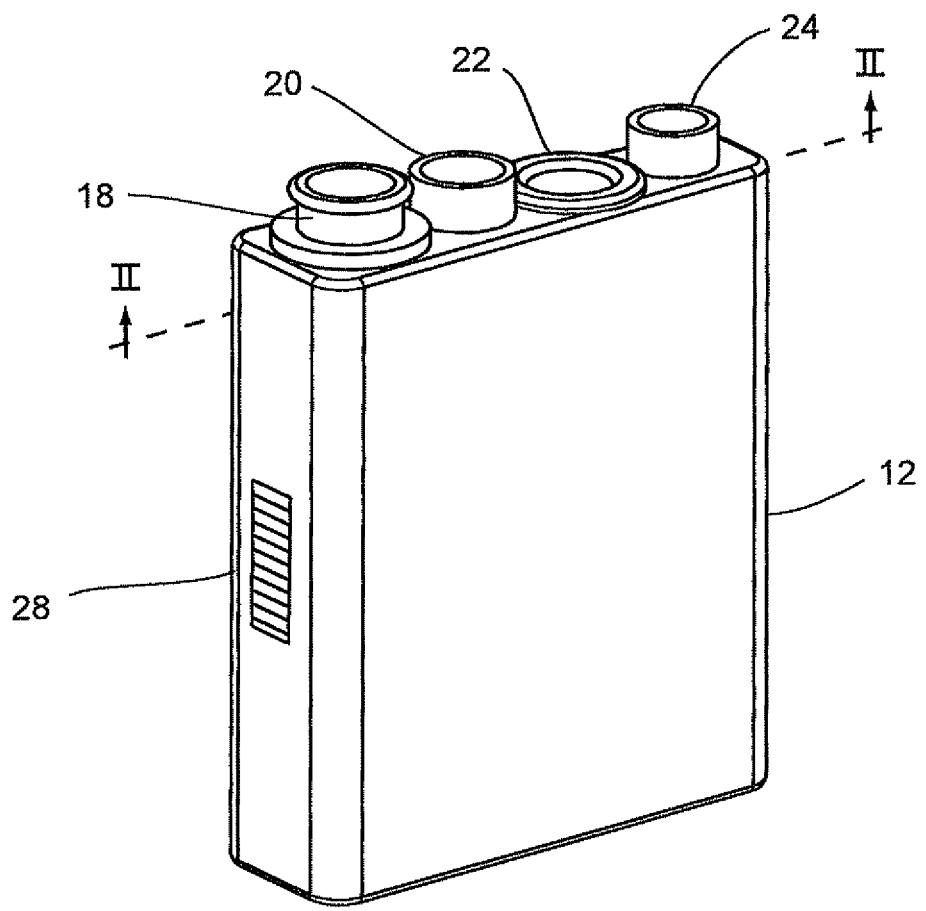
FIG. 1B is a top perspective view of a disposable cartridge used in the magazine shown in FIG. 1A.
Figure 2:
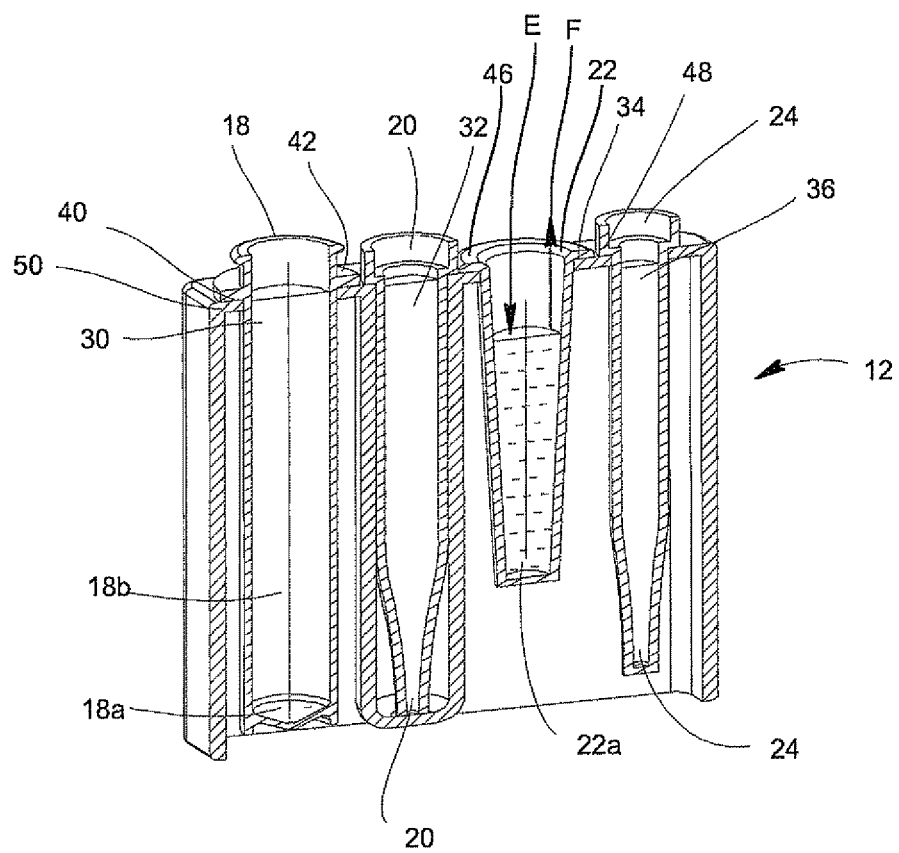
FIG. 2 is a front sectional view illustrating the components of the disposable cartridge of FIG. 1B in phantom.

FIGS. 1A-7 disclose A System for Conducting the Identification of Bacteria in Urine set forth on PCT Application US2008/079533, filed on Oct. 10, 2008, which is commonly owned and herein incorporated by reference in its entirety. Referring to FIGS. 1A, 1B, 2, 3A, 3b, 4A-4C, the system for conducting the identification of bacteria in urine samples includes a disposable cartridge 12 (FIGS. 1B and 2); a sample processor 14 (FIGS. 3A, 3b, 6 and 7); and an optical analyzer 16 (FIGS. 4A, 4B, and 4C). As shown in FIGS. 1A and 2, cartridge 12 contains four disposable components, which are a centrifuge tube 18, a first pipette tip 20 having a 1 ml volume, an optical cup or cuvette 22, and a second pipette tip 24 having a 0.5 ml volume. It is to be understood that the presently described inventive system is appropriate for the identification of bacteria in any fluid and is not limited to bacteria samples contained in urine.

The centrifuge tube 18 is a container that has an elongated body 18b with a tapered end indicated at 18a. In general, the centrifuge tube 18 initially contains the urine sample and the first pipette tip 20 may be used to dilute the urine-dissolved constitutes, and the second pipette tip 24 may be used to transfer the diluted urine sample into the optical cup or cuvette 22 for optical analysis. The disposable cartridge 12 and its disposable components 18, 20, 22, and 24 may be made of a plastic material which is easily molded and inexpensive to manufacture.

Still referring to FIG. 2, the disposable components 18, 20, 22, and 24 are each contained within separate locations 30, 32, 34, and 36, respectively, of the disposable cartridge 12. As is shown, the bottom of compartment 32 which receives and carries the first pipette tip 20 is closed so that any drip from the first pipette tip 20 will not contaminate the surface below the disposable cartridge 12. Each component 18, 20, 22, and 24 is suspended within its respective location 30, 32, 34, and 36 via a lip 40, 42, 46, and 48, respectively, attached to each component 18, 20, 22, and 24, which is supported by the top surface 50 of disposable cartridge 12.

Figure 4A:
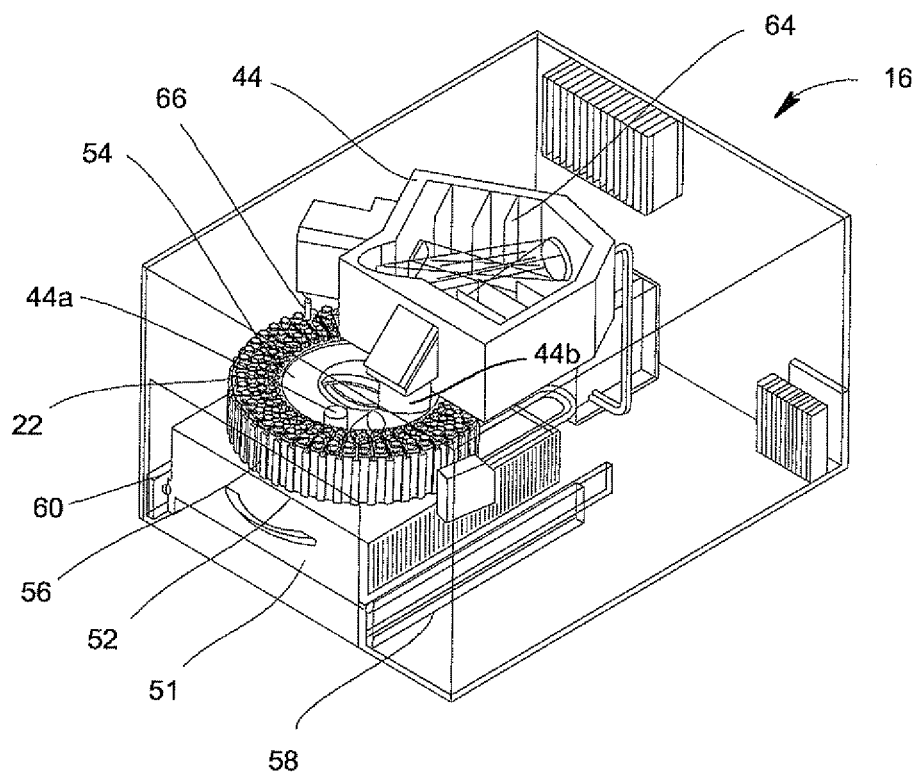
FIG. 4A is a perspective view of an optical analyzer illustrating in phantom the several components of the optical analyzer of the system of the invention.

Referring to FIGS. 2 and 4A, an optical cup or cuvette 22 may be used in the optical analyzer 16 of FIG. 4A. Preferably, the urine samples are prepared with a saline solution since saline solutions minimize background fluorescence while maintaining the integrity of the bacteria which is particularly important when using optics in the urine analysis process. The optical cup or cuvette 22 will include a reflective coating to assist in the optical analysis. The optical cup or cuvette 22 may be made of an ABS plastic material, glass or a metallic material, e.g., aluminum, and then coated with or layered with the reflective material. Alternatively, in the manufacturing of the optical cup or cuvette 22, the layer of reflective material may be incorporated onto the plastic, glass or metallic material. As best shown in FIG. 2, the optical cup or cuvette 22 includes a tapered end indicated at 22a in order to assist with the optical analysis. It is anticipated that the UV-light source in the optical analyzer 16 (FIGS. 4A, 4B and 4C) be directed down the middle of the cup or cuvette 22 for the optical analysis of the urine specimen in the cup or cuvette 22.

Figure 3A:
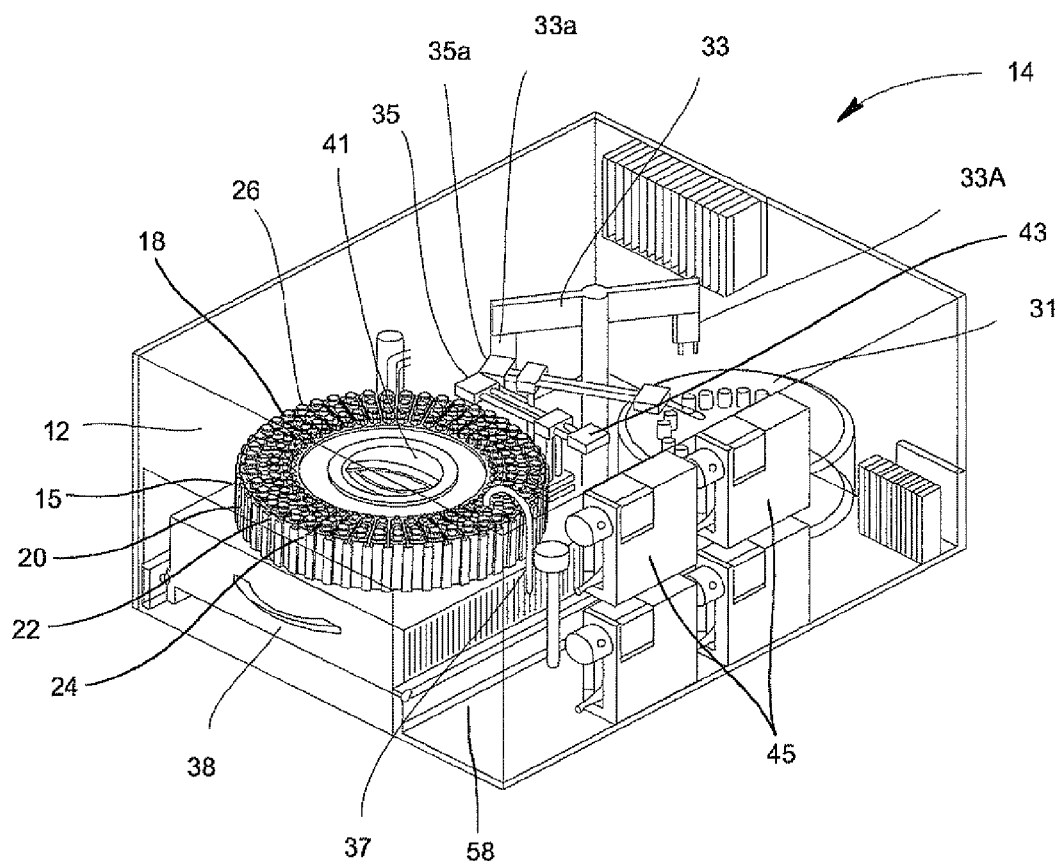
FIG. 3A is a perspective view of a sample processor illustrating in phantom the several components of the sample processor of the system of the invention.

Several disposable cartridges 12 each containing the four disposable components 18, 20, 22, and 24 are then inserted into a magazine 26 shown at the top of FIG. 1A, which is then loaded into the sample processor 14 as shown in FIG. 3A. Magazine 26 contains several disposable cartridges 12 some of which are numbered, each cartridge 12 having a unique bar code as indicated at 28 in FIG. 1A that is paired with the specimen of a patient. Alternatively, the magazine 26 can then be inserted into a device for the optical analysis of the urine samples. Preferably, the same magazine 26 used in obtaining processed urine samples in a sample processor is used in the device for the optical analysis of the processed urine samples.

Figure 3B:
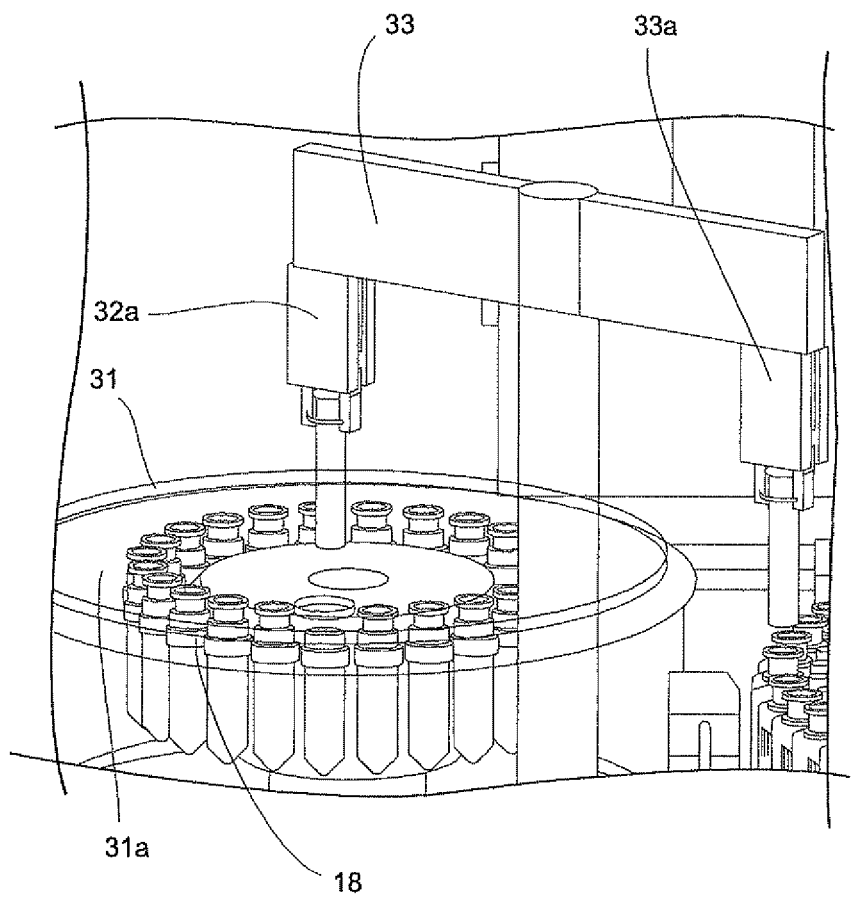
FIG. 3B is an additional perspective view of a sample processor illustrating in phantom the several components of the sample processor of the system of the invention.

The sample processor 14 of FIGS. 3A and 3B contains a centrifuge 31, a carousel 15 containing several disposable cartridges 12; a rotatable table 41 supporting the carousel 15; an optical cuvette 22; a rotatable gripper mechanism 33 which picks up the centrifuge tube 18 (FIGS. 1A and 1B) of each disposable cartridge 12 and inserts the centrifuge tube 18 into the centrifuge 31; two movable fluid transfer arms 35, 35a which are used to dilute the dissolved material in the urine samples via the pipette tip 20 (FIGS. 1B and 2) and to transfer the diluted sample to the optical cup or cuvette 22 (FIG. 2) via the pipette tip 24; and a syringe pump dispenser fluid system 37 for delivering water to the samples for dilution purposes. The sample processor 14 also includes a drawer 38 which has a rotatable table 41 which receives, supports, and rotates the magazine 26 when the drawer 38 is inserted into the sample processor 14. The drawer 38 contains a magazine drive mechanism (not shown) which rotates the magazine 26. The sample processor additionally includes a centrifuge 31 for receiving centrifuge tubes 18 for centrifuging the samples in the tubes 18; two movable fluid transfer arms 35 and 35a for diluting the dissolved material in the saline; and a syringe pump dispenser fluid system 37 for delivering clean fluid to the samples for the dilution of the samples. Control unit 27 shown to the right of FIG. 3A houses controls for ventilation, filtration and power management for the sample processor 14.

The sample processor 14 also includes a drawer 38 for inserting carousel 15 into the sample processor 14, a bar code reader 58 for identification of cartridges 12, a pipetting system 43, and a metering system 45 for managing the pipetting system 43 and dispenser fluid system 37.

In general, centrifuge tube 18 contains about a 2 ml sample of filtered urine which is placed into the centrifuge tube by the user. This sample may then be sufficiently diluted with a saline solution or water by centrifuging the sample followed by using the first pipette tip 20 with the 1.0 ml volume to decant the supernates in two decant cycles followed by refilling of the centrifuge tube 18 with a saline or water. The second pipette tip 24 having the 0.5 ml volume may then be used to draw out about 500 µl of fluid from centrifuge tube 18 and then to dispense this 500 µl of fluid into the respective optical cup or cuvette 22 of the designated patient. This second pipette tip 24 can then be inserted into the first pipette tip 20 and both pipette tips 20, 24 can be disposed of properly. It is believed that one pipette tip may be used to dilute and draw out instead of two pipette tips. This process may be done manually or may be done automatically.

The loading and unloading of the magazine 26 is accomplished with the several disposable cartridges 12 mounted on the rotatable table 41 (FIG. 1A). The manual drawer contains a magazine drive mechanism (not shown). Once the magazine 26 is inserted into the sample processor 14, the drive mechanism (not shown) for rotatable table 41 rotates the magazine 26; the bar code reader (element 58 in FIG. 4A) inventories the samples, a level sensor (not shown) verifies that samples were dosed properly; and a second sensor (not shown) verifies that all of the necessary disposable components 18, 20, 22, and 24 (FIG. 2) are contained in each disposable cartridge 12.

The transfer of the centrifuge tube 18 (FIG. 2) into the centrifuge 31 (FIGS. 3A and 3B) will now be described. A centrifuge lid 31a of the centrifuge 31 is oriented to allow the rotatable gripper mechanism unit 33 to access and load the centrifuge 31. The drive mechanism of the rotatable table 41 is configured to align the centrifuge tube 18 of each disposable cartridge 12 into position relative to the rotatable gripper mechanisms unit 33. The gripper 33a of rotatable gripper mechanism 33 selects the centrifuge tube 18 for transfer from the magazine 26 and into the centrifuge 31. The centrifuge rotor (not shown) is configured to align a vacant centrifuge holder of centrifuge 31 in the load position. The gripper 33a referred to as a "Theta Z gripper" is a radial member that rotates and has a downward and upward movement for picking up and setting a centrifuge tube 18 into a vacant centrifuge holder of centrifuge 31. The lid 31a of centrifuge 31 is closed after all of the centrifuge tubes 18 are placed into the centrifuge 31.

Centrifuge 31 (FIG. 6) is automatically operated to spin the centrifuge tubes 18 at about a 12,000 g-force for about 2 minutes. The centrifuge 31 includes tube holders that are configured to swing each of the centrifuge tubes 18 about 90 degrees upon rotation of the centrifuge 31. The centrifuge allows for precise positioning and position tracking so that correct tubes are returned to cartridges in the magazine after centrifugation. This action results in the solid formation of the bacteria present in the urine sample at the bottom of the centrifuge tube 18.

There are two fluid transfer arms 35, 35a (FIGS. 3A and 3B) for removing the supernates from two samples of two disposable cartridges 12 at a time. After the two fluid transfer arms 35, 35a (FIGS. 3A and 3B) obtain the pipette tip 20 (FIG. 2) with a 1 ml volume, each of the fluid transfer arms 35 and 35a (FIGS. 3A and 3B) makes two consecutive trips to the centrifuge tube 18, each time drawing fluid from the tube 18 and dispensing this fluid into a waste port (not shown) of sample processor 14 before returning the pipette tip 20 to its location on the disposable cartridge that is being sampled and before continuing with the next sample in the disposable cartridge 12 that is rotated to be registered in the sampling location of sample processor 14.

Figure 7:
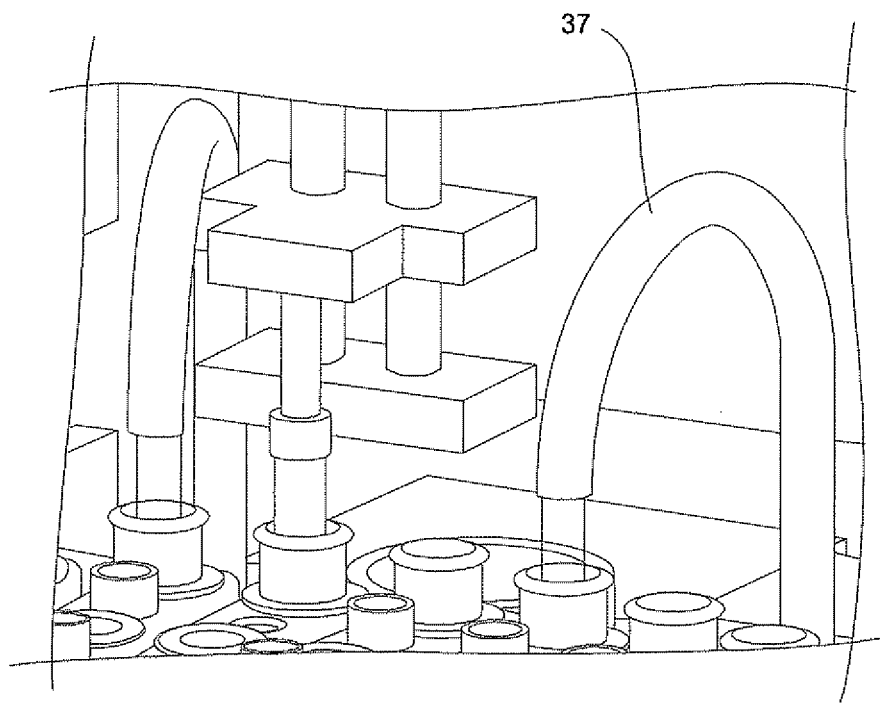
FIG. 7 is an additional perspective view of a sample processor illustrating in phantom the several components of the sample processor of the system of the invention.

The syringe pump dispenser fluid system 37, is illustrated in FIG. 7, for delivering water or saline to the samples for dilution purposes. The waste fluid which had been decanted from a centrifuge tube 18 as described in the preceding paragraph is replaced with clean process fluid via system 37. Two syringe pumps dispense this clean process fluid into the centrifuge tube 18 from which the waste fluid had been removed in the previous step. During the final refill step, a smaller amount of clean fluid is used in order to get the bacteria level in the centrifuge tube 18 to the required concentration.

After the sample in centrifuge tube 18 has been sufficiently diluted with the clean fluid, one of the two fluid transfer arms 35, 35a (FIGS. 3A and 3B) transfers the processed sample in centrifuge tube 18 to the optical cup or cuvette 22 of its respective disposable cartridge 12. One of the fluid transfer arms 35, 35a grasps the pipette tip 24 having the 0.5 ml volume, which until now has not been used in this process. This pipette tip 24 with the smaller volume is used to draw out about 500 µl of fluid from centrifuge tube 18 and is used to dispense this fluid into the respective optical cup or cuvette 22 of the designated patient. This pipette tip 24 with the smaller volume is then inserted into the pipette tip 20 with the larger volume via the fluid transfer arm 35 or 35a for disposal of both pipette tips 20, 24.

The metering/decanting, metering/refilling, and metering/fluid transferring process described herein is to obtain preferably, approximately a 1,000,000:1 dilution of the dissolved materials retaining bacteria in the urine sample in centrifuge tube 18. This can be achieved by 1) centrifuging through means known to those skilled in the art, the urine sample at a 12,000 g-force; 2) decanting about 95% of the fluid by using the first pipette tip 20; 3) replacing the decanted solution of 2) with a saline solution; and 4) repeating steps 1), 2), and 3) at least five times by using the first pipette tip 20. The final processed urine sample in centrifuge tube 18 can then be decanted via the second pipette tip 24 into the optical cup or cuvette 22.

The final processed urine sample in optical cup or cuvette 22 can then be used in an optical analysis for determining the micro-organism's identity and/or quantity in the urine sample in optical cup or cuvette 22. This information can be obtained by using the system as disclosed in the aforesaid U.S. Publication No. 2007/0037135 A1.

Each of the steps described above for one centrifuge tube 18 is done in the sample processor 14 for each of the disposable cartridges 12 in magazine 26. It is to be appreciated that the waste fluid of each disposable cartridge 12 is disposed into a receptacle (not shown) in sample processor 14 or is plumbed directly into a drain. The waste disposables, i.e., the disposable cartridge 12 and disposable components 18, 20, 22, and 24 remain on the magazine 26 for manual removal when the magazine 26 is unloaded in preparation for the next operation of the sample processor 14 for processing the next batch of urine samples.

Figure 4B:
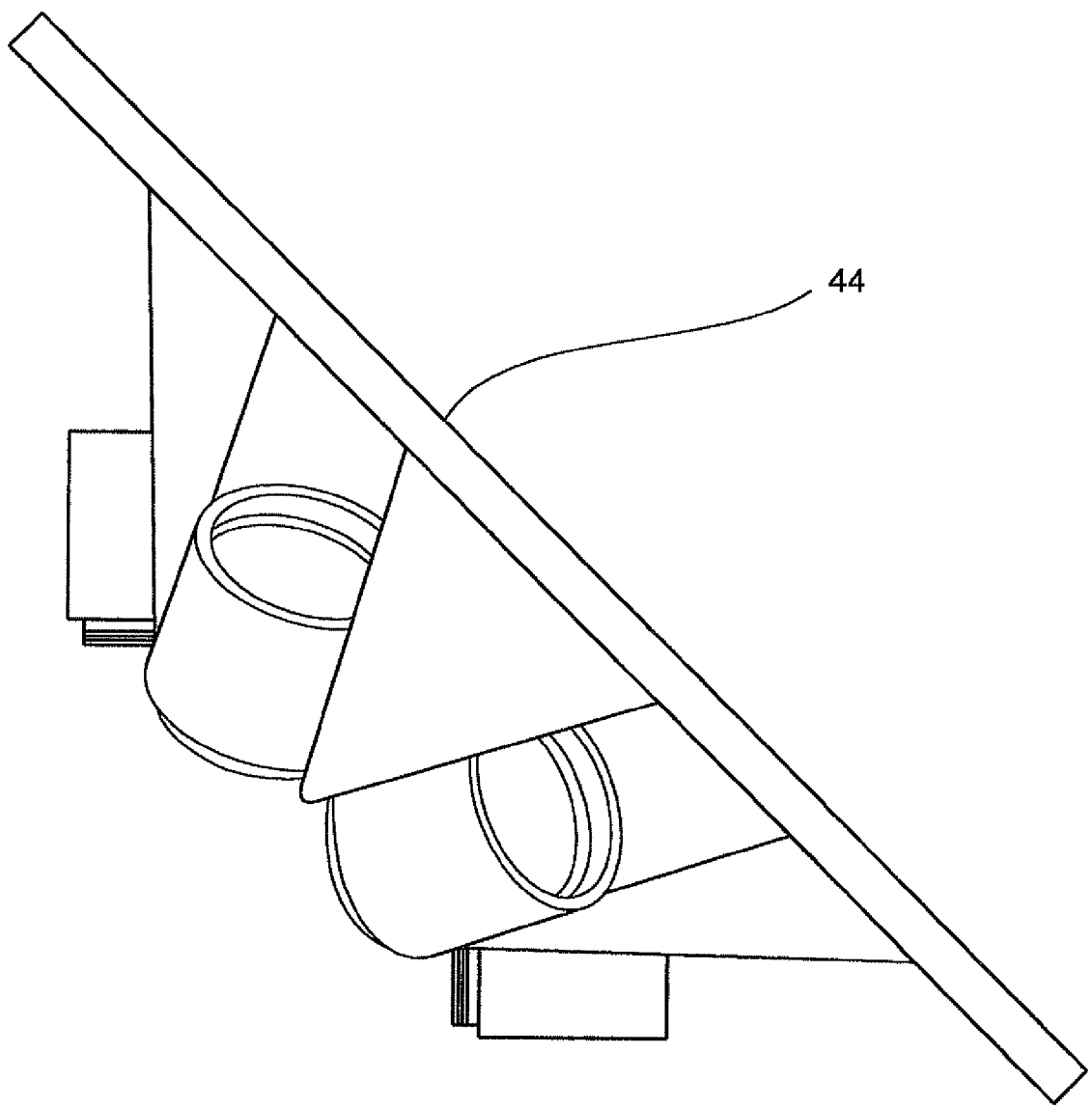
FIG. 4B is a perspective view of an optics system illustrating in phantom the several components of the optics of the system of the invention.
Figure 4C:
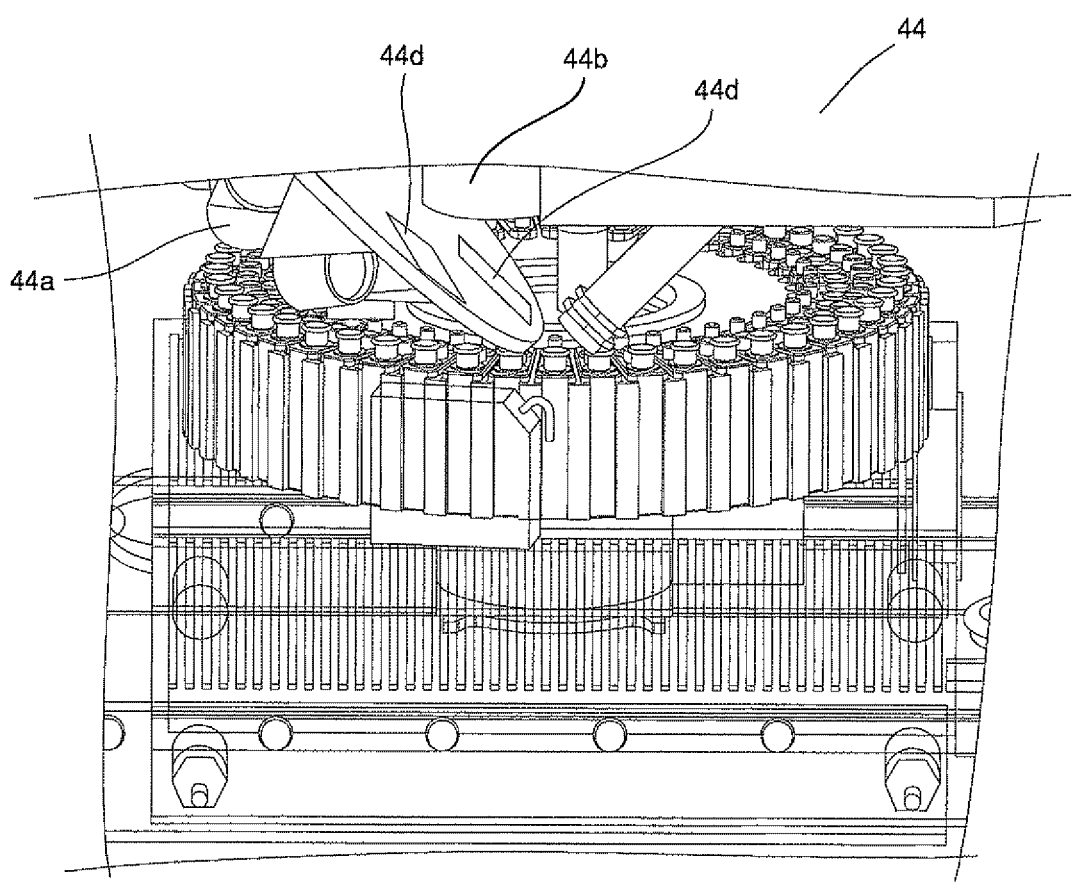
FIG. 4C is an additional perspective view of an optical analyzer illustrating in phantom the several components of the optical analyzer of the system of the invention.

The following steps are involved in processing the urine samples in preparation for analysis via the optical analyzer 16 of FIGS. 4A, 4B, and 4C. In general, a sample of urine is obtained in a test tube. This sample is passed through a 10 micron filter from which a 2 ml sample is obtained and placed into the centrifuge tube 18. The desired diluted sample, i.e., 1,000,000:1 dilution of dissolved materials while retaining bacteria in the urine sample is obtained by centrifuging this 2 ml sample at about a 12,000 g-force; and decanting 95% of the fluid. This latter step is repeated five times wherein the decanted solution is replaced each time with a saline solution. A saline solution is selected for this process in that it minimizes background fluorescence which comes into play when the processed urine sample is inserted into the optical analyzer 16 while maintaining the bacteria integrity.

Figure 8A:
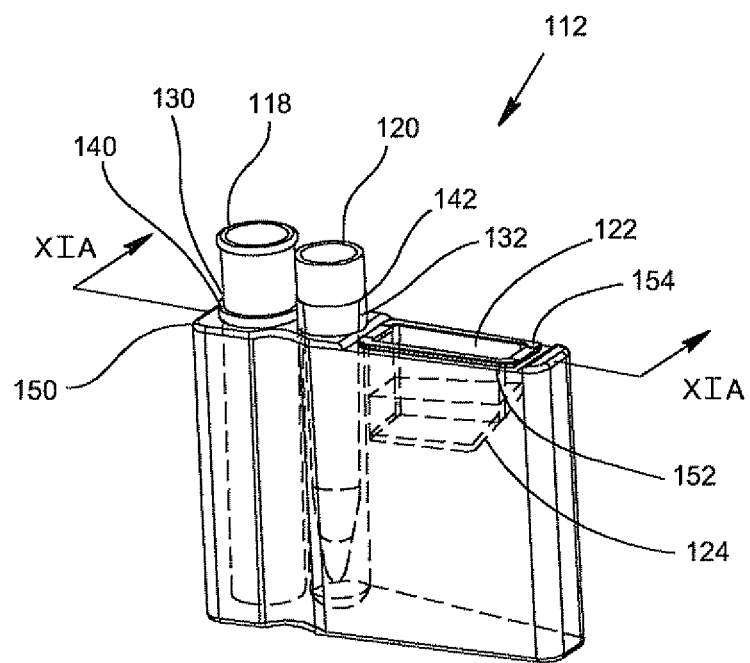
FIG. 8A is a perspective view of a disposable cartridge according to an alternative embodiment of the invention for supporting the disposable components including an optics cup.
Figure 8B:
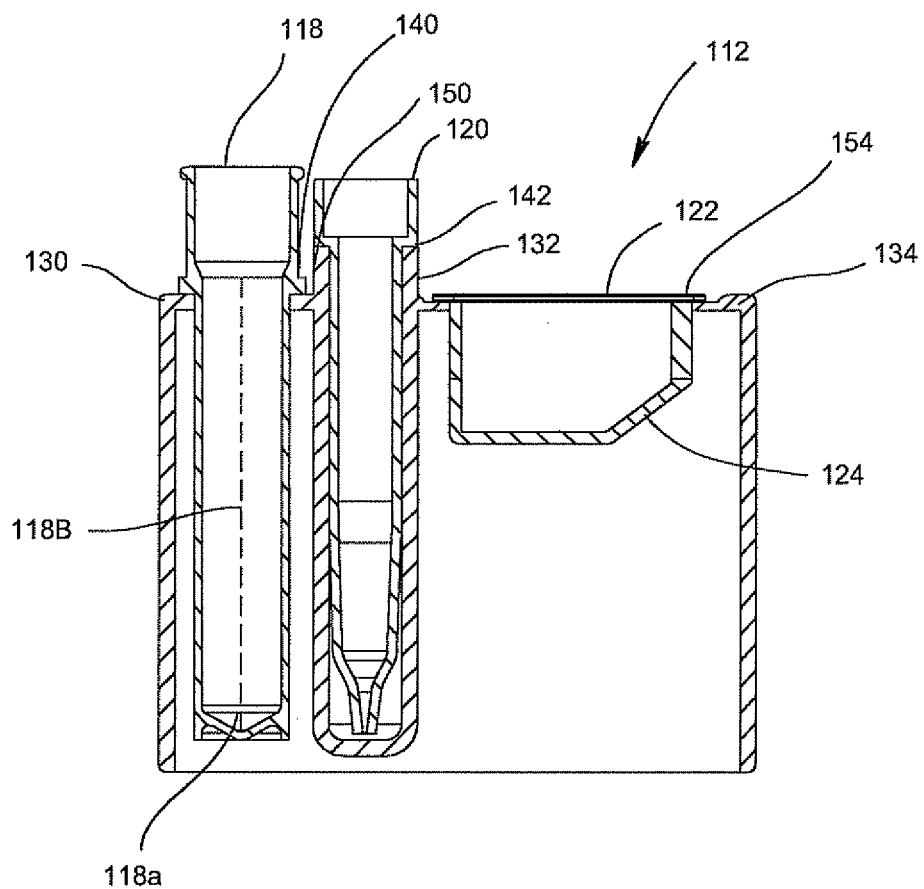
FIG. 8B is a cross sectional view taken along line IX A-IX A, illustrating the disposable cartridge of FIG. 8A and the disposable components including an optics cup which is shown in phantom.
Figure 8C:
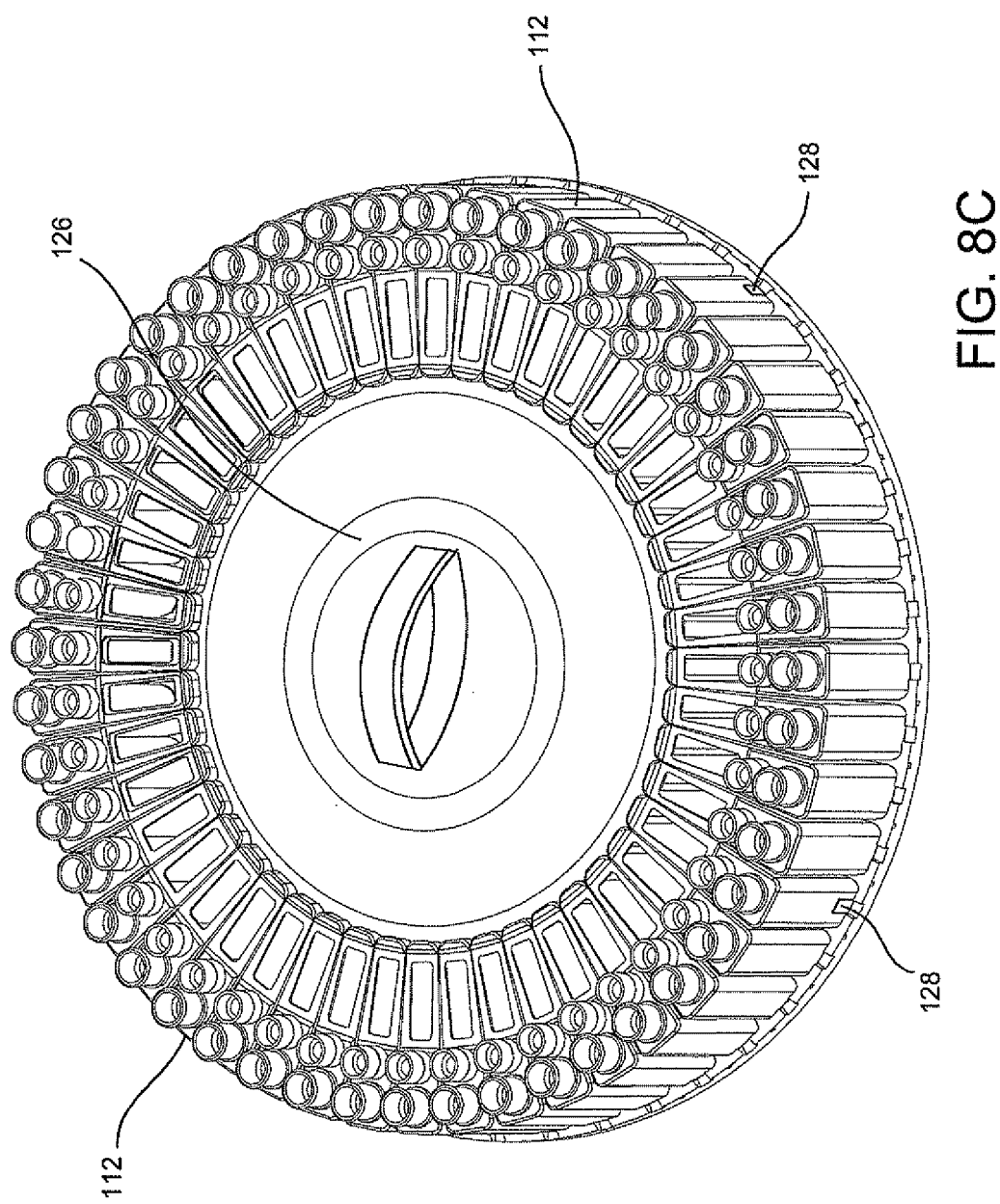
FIG. 8C is a top perspective view of a magazine having a plurality of the disposable cartridges of FIGS. 8A and 8B.

Referring to FIGS. 8A, 8B, and 8C, there is shown an alternative embodiment for a disposable cartridge generally indicated as 112, which may be used for conducting the identification and quantification of contaminants, e.g., micro-organisms, e.g., bacteria in samples, e.g., urine samples. Disposable cartridge 112 contains and carries several disposable components which include a centrifuge tube 118, a pipette tip 120 and an optics cup or cuvette 122. With particular reference to FIG. 8B, the pipette tip 120 has a predetermined volume, for example, ranging between 0.1 ml to about 10 ml, preferably 1 ml to 2 ml. The centrifuge tube 118 is a container that has an elongated body 118b with a tapered end indicated at 118a. In general, the centrifuge tube 118 initially contains the sample and the pipette tip 120 may be used to dilute the dissolved sample constituents and then transfer the diluted urine sample into the optics cup or cuvette 122 for optical analysis. The disposable cartridge 112 and its disposable components 118, 120, and 122 may be made of an ABS plastic material which is easily injection molded and inexpensive to manufacture.

Still referring to FIGS. 8A and 8B, the disposable components 118, 120, and 122 are each contained within separate compartments 130, 132, and 134, respectively, of the disposable cartridge 112. As is shown, the bottom of compartment 132 which receives and carries the pipette tip 120 is closed so that any drip from the pipette tip 120 will not contaminate the surface below the disposable cartridge 112. Components 118 and 120 are suspended within its respective compartment 130, 132 via a lip 140, 142, respectively. Lips 140 and 142 are attached to its respective component 118 and 120, and are supported by a top surface 150 of disposable cartridge 112. In a similar manner, optics cup or cuvette 122 is suspended within its respective compartment 134 via a flange 154 of optics cup or cuvette 122 which the flange 154 is supported by the top surface 150 of disposable cartridge 112. The compartments 130 and 132 are generally cylindrical shaped and extend substantially the length of centrifuge tube 118 and pipette tip 120. Compartment 134 for positioning supporting optics cup or cuvette 122 is substantially enclosed within the disposable cartridge 112 and has a configuration similar to that of optics cup or cuvette 122.

Figure 9A:
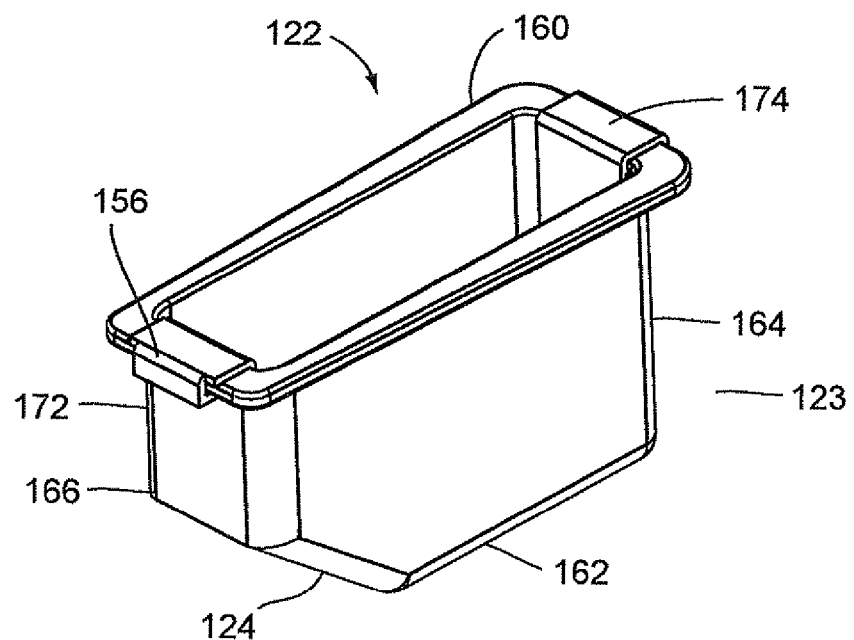
FIG. 9A is a perspective view illustrating an optics cup of the present invention with an aluminum ribbon liner partially covering the inner surface of the container of the optics cup.
Figure 9B:
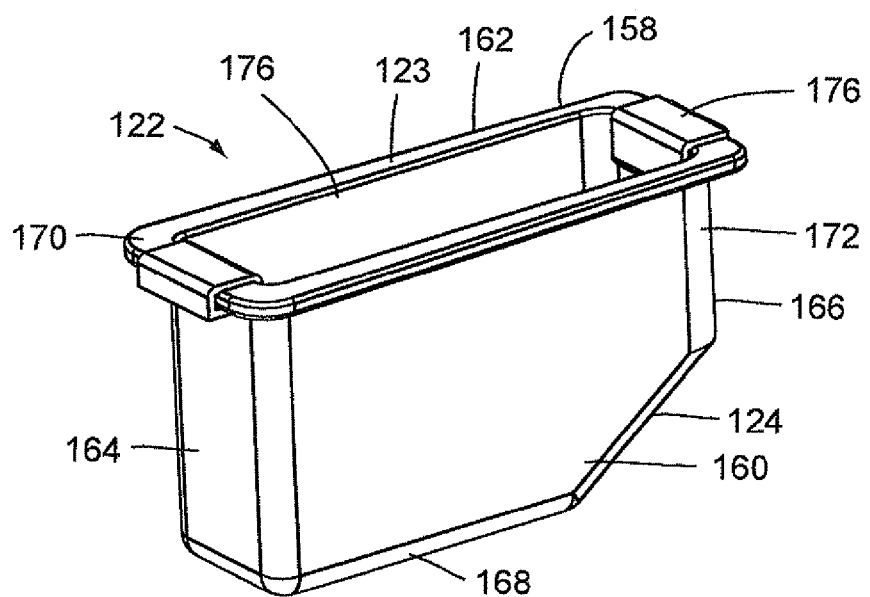
FIG. 9B is a perspective view illustrating an optics cup of the present invention with an aluminum liner totally covering the inner surface of the container.

The optics cup or cuvette 122 is a container and preferably includes a reflective coating or layer to assist in the optical analysis. The optics cup or cuvette 122 is shown in FIGS. 9A and 9B and is discussed in further detail below. In particular, an inner surface of optics cup or cuvette 122 is coated with a reflective material or contains a layer of reflective material. The optics cup or cuvette 122 may be made of a non-reflective material, for example, an ABS plastic material or glass or it may be made of a metallic material, e.g., aluminum. In the latter instance, that is, if the optics cup or cuvette 122 is made of a non-reflective material, it may be coated with or layered with the reflective material. Alternatively, in the manufacturing of the optics cup or cuvette 122, the layer of reflective material may be incorporated onto the plastic or glass. As best shown in FIG. 9A, the optics cup or cuvette 122 includes the lower tapered area indicated at 124 in order to assist with the optical analysis of the specimen, and it is anticipated that the UV-light source provided in an optical analysis be directed into the optics cup or cuvette 122 for the optical analysis of the specimen, more about which is discussed herein below.

The disposable cartridge 112 preferably is injection molded and made of an ABS plastic, preferably a non-reflective black colored plastic. The disposable cartridge 112 contains compartments 130, 132, and 134 for positioning and supporting the centrifuge tube 118, pipette tip 120, and optics cup or cuvette 122 discussed hereinabove. The compartments 130 and 132 generally are cylindrical in shape so as to receive the cylindrical shapes of the centrifuge tube 118 and pipette tip 120 for adequate support of centrifuge tube 118 and pipette tip 120 within the disposable cartridge 112. However, the compartment 134 for positioning and supporting the optics cup or cuvette 122, particularly if the optics cup or cuvette 122 is rectangular-shaped, need not be molded in the same configuration as the optics cup or cuvette 122. In this instance, the compartment 134 for supporting the optics cup or cuvette 122 in disposable cartridge 112 may, in general, include a rectangular-shaped opening 158 (FIG. 8A) located in the top surface 150 of the disposable cartridge 112 wherein the top flange 154 of optics cup or cuvette 122 engages and is supported by the top surface 150 of disposable cartridge 112 and the optics cup or cuvette 122 is suspended in the disposable cartridge. Alternatively, compartment 134 for positioning and supporting optics cup or cuvette 122 may be totally enclosed and may have a similar configuration to that of rectangular-shaped optics cup or cuvette 122.

As discussed above and shown in FIG. 8C, several disposable cartridges 112 each containing disposable components 118, 120, and 122 may be inserted into a magazine 126, which may then be inserted into a sample processor 14 such as the processor shown in FIG. 3A. Each disposable cartridge 112 can have a unique bar code 128 which is paired with the initial specimen of a patient. Alternatively, the magazine 126 may then be inserted into a device such as the optical analyzer 16 shown in FIG. 4A for the optical analysis of the samples. Preferably, the same carousel used in obtaining processed urine samples in a sample processor is used in the device for the optical analysis of the processed samples.

Figure 8D:
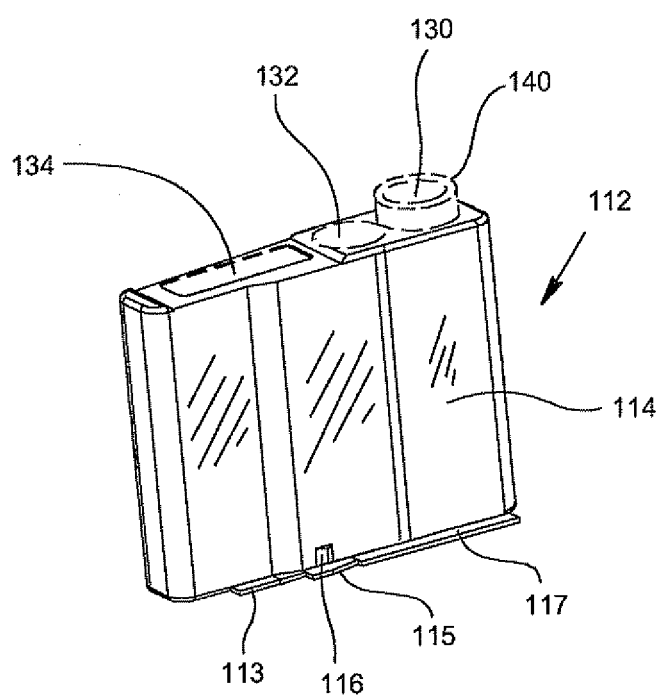
FIG. 8D is a perspective view of the disposable cartridge without disposable components of FIG. 8A showing attachment clips for securing the cartridge within the magazine.
Figure 8E:
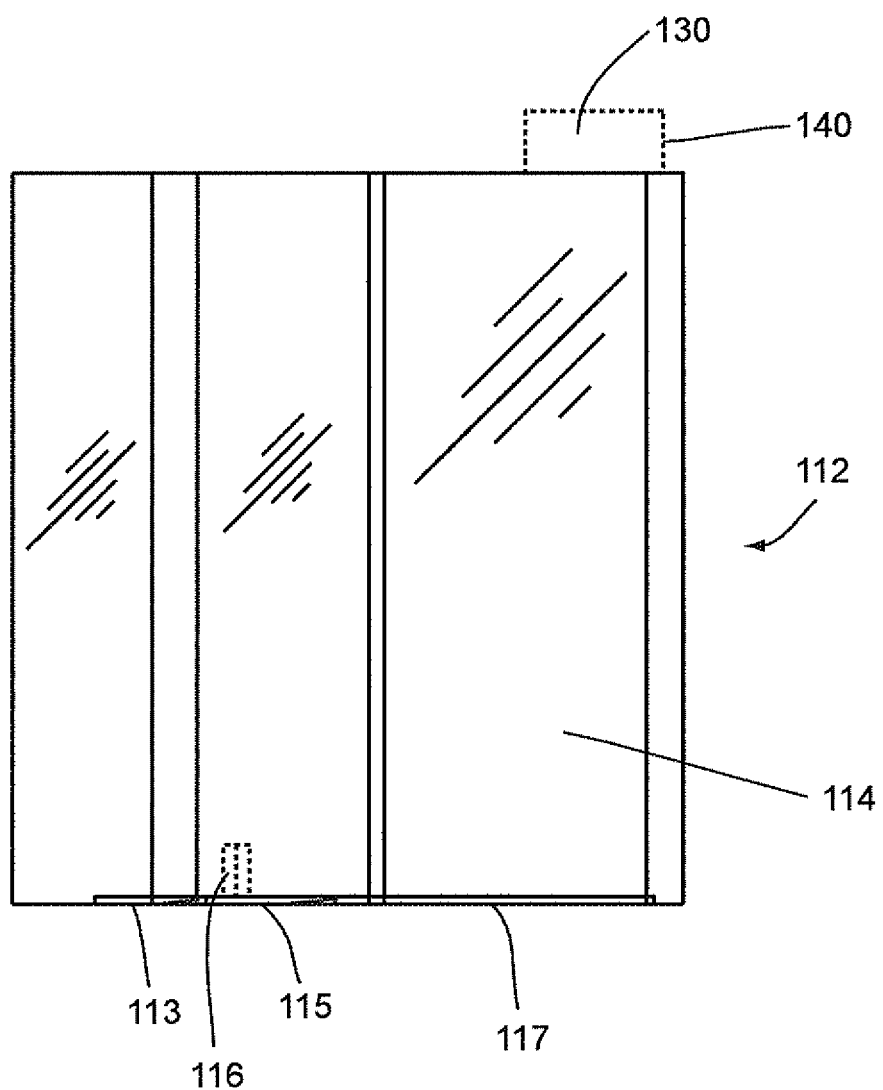
FIG. 8E is a side elevation view of the cartridge of FIG. 8D.
Figure 8F:
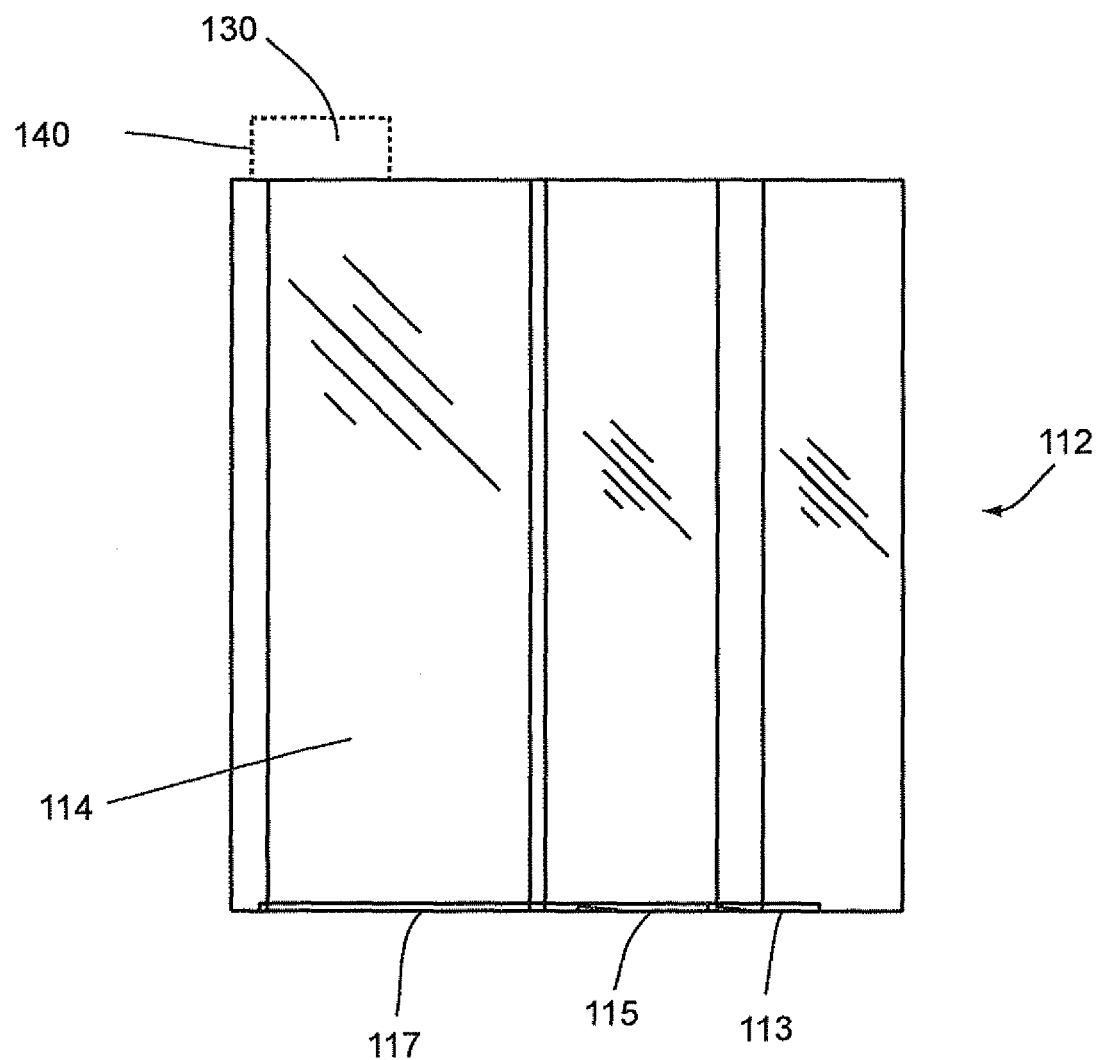
FIG. 8F is an opposite side elevation view of the cartridge of FIG. 8D.

FIGS. 8D, 8E, and 8F show the disposable cartridge 112 without the disposable components 118, 120 and 122 according to an embodiment of the invention wherein attachment clips 113, 115, and 117 are provided. These attachment clips 113, 115, 117 extend in a horizontal direction along a bottom edge portion of a side body portion 114 of the cartridge 112. As shown in FIGS. 8D and 8E, attachment clip 115 may include a vertically extending alignment member 116. This vertically extending member 116 can be used for aligning the cartridge 112 during insertion into the magazine 126. The attachment clips 113, 115, 117 are configured to cooperate with the cartridge openings within the magazine 126, as shown in FIG. 8C, to form a snap fit arrangement therein to attach the cartridge 112 within this opening. Accordingly, in this embodiment, the cartridge openings within the magazine 126 can include appropriate clip openings (not shown) which are configured to cooperate with the clips 113, 115, 117 and alignment member 116 of the cartridge 112.

In general, centrifuge tube 118 may first contain, for example, between 1 ml to about 2 ml sample of a filtered specimen. This sample may then be sufficiently diluted with a saline solution or water by centrifuging the sample followed by using the pipette tip 120 to decant the supernates in two decant cycles followed by refilling of the centrifuge tube 118 with a saline or water. The pipette tip 120 may then be used to draw out a predetermined amount of fluid, e.g., 100 to 500 µl of fluid from centrifuge tube 118 and then to dispense this amount of fluid into its respective optics cup or cuvette 122 of the designated patient.

The metering/decanting, metering/refilling and metering/fluid transferring process described herein in the preceding paragraph may be used to obtain preferably, approximately a 1,000,000:1 dilution of the dissolved material in the sample while retaining contaminants, e.g., bacteria in the sample, e.g., biological sample in centrifuge tube 118. This can be achieved by: 1) centrifuging, through means known to those skilled in the art, the sample at 12,000 g-force; 2) decanting about 95% of the fluid by using the pipette tip 120; 3) replacing the decanted solution of step 2) with a saline solution; and 4) repeating steps 1), 2), and 3) at least five times by using the pipette tip 120. The final processed urine sample in centrifuge tube 118 can then be decanted via the pipette tip 120 into the optics cup or cuvette 122.

The final processed sample in optics cup or cuvette 122 can then be used in an optical analysis for determining the microorganism's identity and/or quantity in the sample. This information can be obtained by using the system as disclosed in the aforesaid U.S. Publication No. 2007/0037135 A1.

FIGS. 9A and 9B illustrate an optics cup or cuvette, generally indicated as 122, including a rectangular-shaped container 123 having a well 156 and a rectangular opening 158 contiguous to well 156 for receiving a fluid sample which is then carried in well 156. As stated above, the optics cup or cuvette 122 may be made of glass or plastic, preferably, an injection molded plastic. The fluid sample may be for example a biological, chemical or toxicant sample, e.g., urine sample which is optically analyzed, for example, for the type and amount of organism or micro-organism, e.g., bacteria in the sample. Well 156 of container 123 is formed by spaced-apart sidewalls 160 and 162, spaced-apart end walls 164 and 166 and a floor 168. Spaced-apart sidewalls 160 and 162 and spaced-apart end walls 164 and 166 form a flange 170 contiguous to the rectangular opening 158. As shown in FIGS. 9A and 9B, the end wall 166 has an upper area 172 and a lower tapered area 124 extending inwardly of upper area 172 of end wall 166 and downwardly relative to upper area 172 of end wall 166 and the rectangular opening 158 such that the length of floor 168 is less than the length of rectangular opening 158.

With particular reference to FIG. 9A, the optics cup or cuvette 122 also includes a ribbon liner 174 which extends the full length of end wall 164, floor 168, upper area 172 of end wall 166 and lower tapered area 124 of end wall 166 to cover the inner surfaces of end wall 164, floor 168, upper area 172 of end wall 166 and lower tapered area 124 of end wall 166. Ribbon liner 174 may be referred to as a "wet" ribbon liner since it comes into contact with the liquid sample from all sides. Ribbon liner 174 is preferably made of a reflective material, for example, aluminum. Ribbon liner 174 may be made from a piece of stamped aluminum which may be pre-shaped to conform to the configuration formed by end wall 164, floor 168, lower tapered area 124 of end wall 166 and upper area 172 of end wall 166 prior to the installation of ribbon liner 174 in well 156.

Optics cup or cuvette 122 may be made of a material known to minimize the leaching of the contaminants from the material that might be excited by the incident light used in an optical analysis of the sample. As stated above, optics cup or cuvette 122 may be injection molded and made of a material, for example, ABS plastic or glass. It is anticipated that the UV light provided in an optical analysis of the sample or specimen in container 123 of optics cup or cuvette 122 be directed into the tapered area 124 of well 156 for the optical analysis of the specimen and be reflected off of the ribbon liner 174, including the lower tapered area 124 of end wall 166. As discussed herein above, the material of optics cup or cuvette 122, the reflective material of ribbon liner 174 and the lower tapered area 124 of end wall 166 work in a synergistic manner to enhance the UV-light reflection to more effectively collect the fluorescence emission of the samples for the identification and quantification of the organism or micro-organism, e.g., bacteria in the samples and at the same time minimize the background fluorescence and/or minimize the contamination of the sample fluid from the container or wetted surfaces of the container. The collection of the fluorescence emission of the sample from the optic cup or cuvette 122 is discussed in greater detail below.

FIG. 9B illustrates that alternatively, optics cup or cuvette 122 may include a full liner 176, if light collection from the sidewalls 160 and 162 as well as from the end wall 164, floor 168, the lower tapered area 124 of end wall 166 and the upper area 172 of end wall 166 is needed for the optical analysis of a sample. This full liner 176 is shaped and formed to substantially clad or cover the inner surfaces of sidewalls 160 and 162, end wall 164, floor 168, lower tapered area 124 of end wall 166 and the upper area 172 of end wall 166. The full liner 176 of FIG. 9B functions similarly to the ribbon liner 174 in well 156 of optics cup or cuvette 122 of FIG. 9A with regard to the UV-light of the optical analyzer.

The ribbon liner 174 of FIG. 9A and full liner 176 of FIG. 9B may be polished to obtain a desired degree of surface roughness for the reflection of the UV-light in optics cup or cuvette 122. The polishing process may either be performed on the reflective material used to form wet ribbon liner 174 or full wet liner 176 either when the reflective material, i.e., aluminum is in raw sheet form prior to the stamping and forming process or when liners 174 and 176 are formed and inserted into optics cup or cuvette 122 via a bulk polishing process. That is, the reflective material may either be polished before the stamping and forming process or the stamped parts may be polished.

Figure 9C:
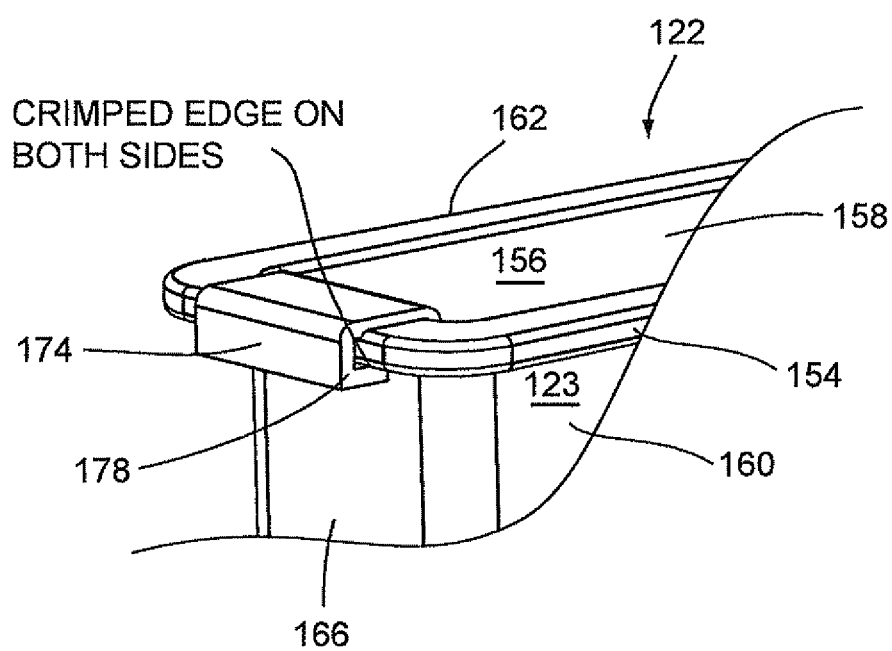
FIG. 9C is a partially enlarged perspective view illustrating a portion of the ribbon liner of FIG. 9A attached via a crimping process to a flange of the optics cup of the present invention.

FIG. 9C illustrates that the wet ribbon liner 174 of FIG. 9A may be secured to optics cup or cuvette 122 via a crimping process. In this instance, the one end 178 of wet ribbon liner 174 is bent to conform around and under the outer contour of the portion of flange 154 formed by end wall 166 and end 178 is fastened to flange 154 via a crimping process which is well known to those skilled in the art. Even though not shown in FIG. 9C, it is to be appreciated that the opposite end of ribbon liner 174 may be bent to conform around and then under the outer contour of the portion of flange 154 formed by end wall 164 and then fastened to flange 154 via a crimping process.

It is to be further appreciated that even though not shown, in the instance a full liner 176 of FIG. 9B is installed in optics cup or cuvette 122, that this liner 176 may be secured to flange 154 via a crimping process. The full liner 176 may be stamped and folded in a progressive die and then singulated for installation in optics cup or cuvette 122. Both liners 174 and 176 may be wound on a reel and the optics cup or cuvette 122 can be easily assembled in an automated manufacturing process. That is, the liners 174 and 176 may be on a reel so that a machine can be fed with the reels and the liners inserted into the optic cups or cuvettes 122.

Figure 10:
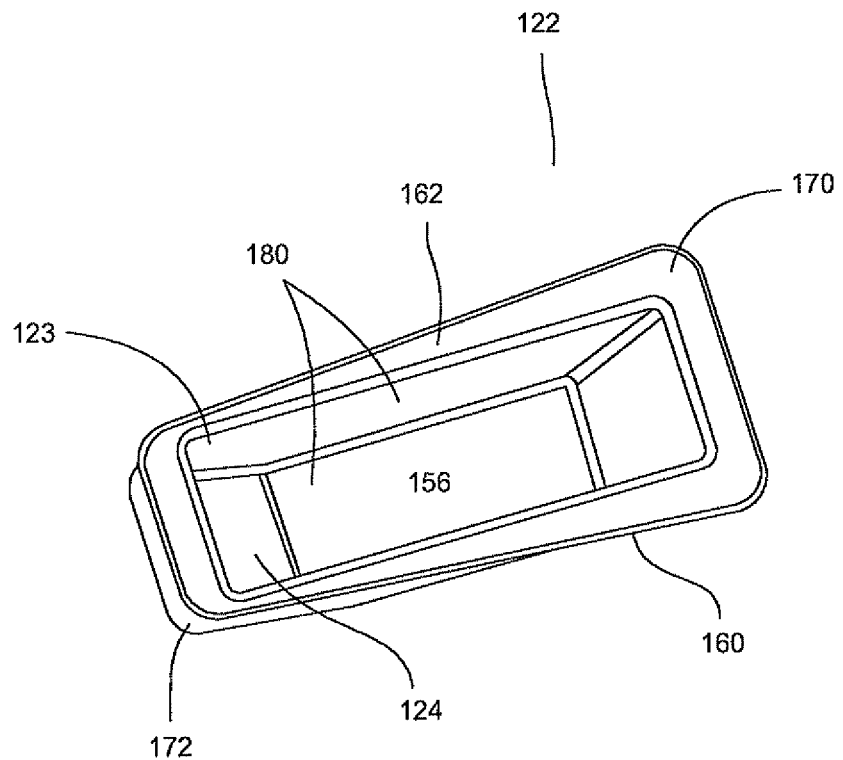
FIG. 10 is a top plan view illustrating the inner surface of the container of FIGS. 9A and 9B as being coated with an aluminum coating.

FIGS. 9A and 9B illustrate a reflective material for optics cup or cuvette 122 as being a separate piece that is manufactured, formed and shaped for insertion or installation into well 156 of container 123. The present invention envisions that instead of liners 174 and 176, optics cup or cuvette 122 may be coated with a thin layer of reflective material as indicated at reference number 180 in FIG. 10. In this embodiment, optics cup or cuvette 122 may be injection molded with the desired surface roughness and then coated with a thin layer of reflective material 180, for example, pure aluminum, by either a vacuum metallization process or by an electroplating process. The industry has shown that it may be difficult to coat inner surfaces of a container that has a certain depth. In this instance, customized electrodes may need to be provided to achieve the desired coverage and uniformity of coating in the well 156 of container 123 of optics cup or cuvette 122. The coating of reflective material 180 may extend totally along the inner surfaces of sidewalls 160 and 162, end walls 164 and 166 and floor 168 of container 123 similar to the full liner 176 of FIG. 9B or the coating may extend partially along the inner surfaces of end wall 164, the floor 168, lower tapered area 124 of end wall 166 and the upper area 172 of end wall 164 of container 123 similar to the ribbon liner 174 of FIG. 9A.

Figure 11A:
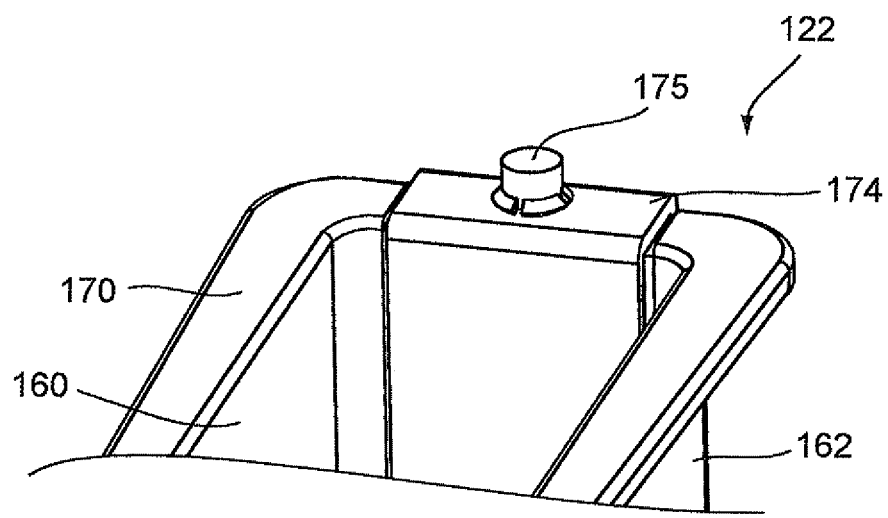
FIG. 11A is a partially enlarged perspective view illustrating the ribbon liner of FIG. 9A being attached to the container via a one-way retention tab.
Figure 11B:
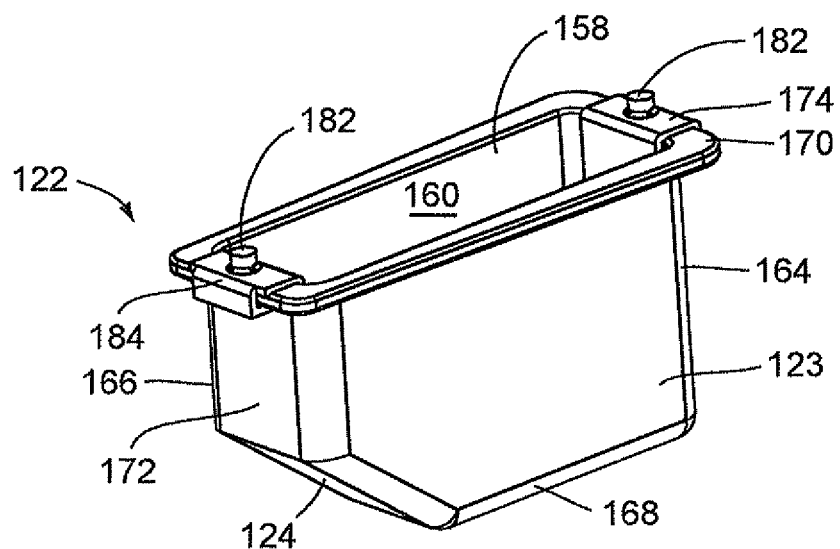
FIG. 11B is a perspective view illustrating the ribbon liner of FIG. 9A being attached to the container via heat staked pins.
Figure 11C:
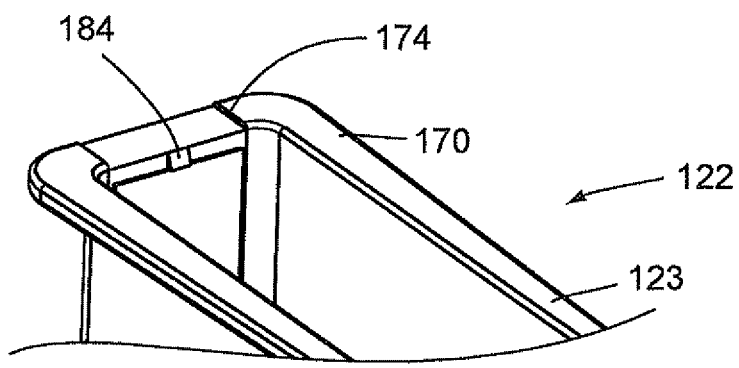
FIG. 11C is an enlarged partial perspective view illustrating the ribbon liner of FIG. 9A being attached to the container via a snap mechanism.

FIGS. 11A, 11B, and 11C illustrate additional systems for securing ribbon liner 174 in container 123 of optics cup or cuvette 122. Specifically, FIG. 11A illustrates that the ribbon liner 174 may be secured to the portion of flange 170 formed by end wall 164 via a one-way retention tab 175 which is inserted through the ribbon liner 174 and flange 170 in a manner known to those skilled in the art. For example, for this one-way retention tab, the container 123 has a post which has small "teeth" and the liner has a hole or opening and once the liner is positioned over the post, the "teeth" of the post prevent the liner from being moved and, therefore, slipping out of container 123. Even though not shown, it is to be appreciated that the opposite end of ribbon liner 174 may also be attached to the portion of flange 170 formed by end wall 166 in a similar manner.

FIG. 11B specifically shows that the one end of ribbon liner 174 may be secured to the portion of flange 170 formed by end wall 164 and that the opposite end of ribbon liner 174 may be secured to the portion of flange 170 formed by end wall 166 via heat staked pins 182 and 184. Heat staked pins 182, 184 are also known to those skilled in the art. For example, in general, a heat stake pin 182, 184 is generally smooth and once the ribbon liner 174 is positioned on the pin 182, 184, heat is used to deform the end so that the ribbon liner 174 is prevented from slipping out of the container 123.

FIG. 11C specifically shows that the one end of ribbon liner 174 may be secured in end wall 164 near flange 170 via a snap mechanism 186. This snap mechanism 186 may be formed in end wall 164 by stripping the molded material with a tool. If ribbon liner 174 is made of aluminum, ribbon liner 174 can be held securely in snap mechanism 186 since aluminum is flexible enough that it can be easily snapped into snap mechanism 186. Even though not shown in FIG. 11C, it is to be appreciated that end wall 166 also includes a similar snap mechanism 186 for securing the opposite end of ribbon liner 174 in container 123 of optics cup or cuvette 122.

Figure 12:
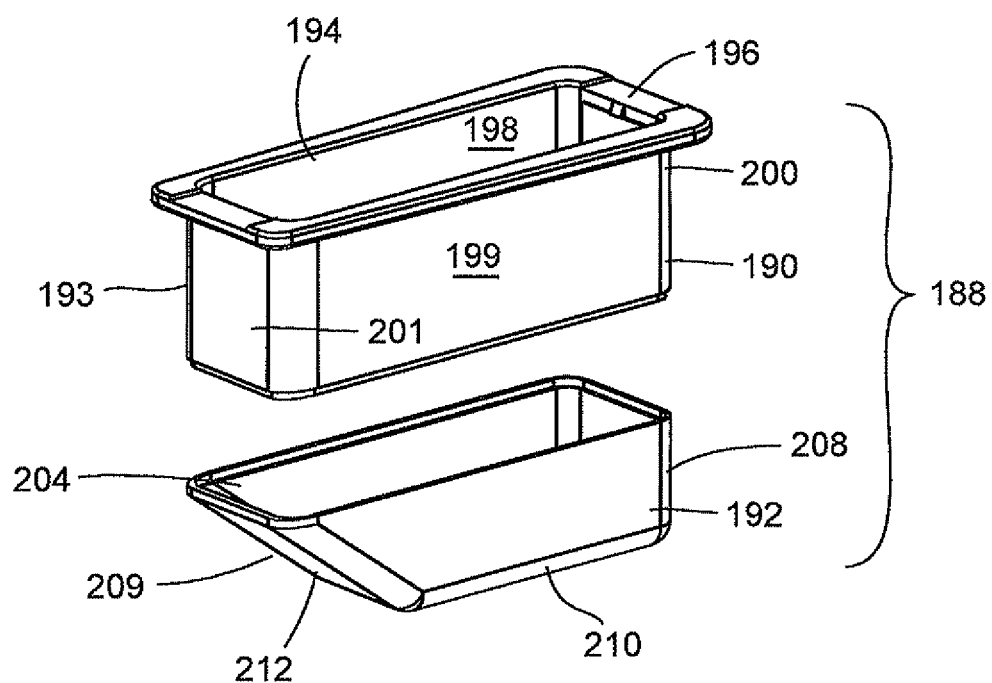
FIG. 12 is a perspective view illustrating a further embodiment for a rectangular-shaped container of the present invention.

FIG. 12 illustrates an optics cup or cuvette 188 having a two-piece construction including an upper piece 190 and a lower piece 192. As shown, the upper piece 190 has a rectangular body 193 having a rectangular opening 194 contiguous to flange 196, which in turn, is formed by spaced apart sidewalls 198 and 199 and end walls 200 and 201. Even though not shown, upper piece 190 is also fully opened at the bottom and has an indented portion 202. The lower piece 192 has a rectangular opening 204 formed by spaced apart sidewalls 206 and 207 and end walls 208 and 209, and a floor 210. End wall 209 of lower piece 192 has a tapered area 212 for re-directing the light. Tapered area 212 extends down from the rectangular opening 194 and extends downwardly to floor 210, thereby making the length of floor 210 less than the length of rectangular opening 204.

Both upper piece 190 and lower piece 192 are joined together via indented portion 202 fitting into the rectangular opening 204 of lower piece 192 and these two pieces 190 and 192 may be bonded together via a method selected from the group consisting of an ultrasonic, butt welding process; an ultrasonic, shear welding process; a press fit process; a snap fit process; and a solvent welding process using either a press or snap fit for fixing the two pieces 190 and 192 together during the bonding process. In this instance, the lower piece 192 is sufficiently shallow as to enable the desired critical optical inner surfaces of spaced apart sidewalls 206 and 207, end walls 208 and 209 and floor 210 of lower piece 192 to be coated with a reflective material 180, such as aluminum, preferably via a vacuum metallization process in a cost-effective manner compared to some of the disadvantages in using an optics cup or cuvette 122 with a deep well 156 as discussed hereinabove with reference to FIG. 10. The upper piece 190 may be regarded as a skirt or a slosh shield thereby preventing the sample from flowing out of the optics cup or cuvette 188.

As may be appreciated, the upper flanges of optics cup or cuvette 122 and 188 of the present invention may be used for supporting the optics cup or cuvette 122, 188 on a top surface 150 of a disposable cartridge 112 used in magazines 126 for processing the samples and then optically analyzing the samples. Also, the reflective surfaces of the optics cup or cuvette 122 and 188 are such that the UV light from the optical analyzer can be directed down into the cups or cuvettes and reflected off of the reflective surfaces and tapered areas as discussed in detail below to more efficiently and effectively produce the fluorescence emission necessary in obtaining the required information for optically analyzing the specimens for the identification and quantification of, for example, organisms or micro-organism, e.g. bacteria in the specimens, e.g., urine specimens.

The optical analyzer 16 of FIGS. 4A, 4B, and 4C, as disclosed in PCT Application US2008/079533 will now be described. While the drawings show cartridges 12 according to the embodiment illustrated in FIGS. 1A, 1B, and 2, it is recognized that the alternative cartridge of FIGS. 8A and 8F along with the cup or cuvette design 122 and/or 188 of FIGS. 9A-9C, 10, 11A-11C and 12 can also be utilized with the optical analyzer 16. With reference to FIG. 4A, the optical analyzer 16 includes an optics system 44 (shown in greater detail in FIGS. 4B and 4C), a thermal control unit (not shown), a drawer 51 which has a rotatable table 52 which receives, supports, and rotates a magazine 54 containing a plurality of holders 56 for receiving the disposable cartridges 12 in which optics cups or cuvettes 22 contain the processed urine samples which are to be analyzed, and a bar code reader 58 (FIG. 4A).

As can be appreciated, a cartridge 12 or 112 that has the optics cups or cuvettes 22, 122 or 128 containing the processed urine sample for optical analysis are placed into the holders 56 of the magazine 54. FIG. 4A illustrates the magazine 54 mounted on the rotatable table 52 being loaded into the optical analyzer 16. Drawer 51 is pulled out manually for the loading and unloading of magazine 54. Drawer 51 contains the thermal control unit (not shown) and a drive mechanism (not shown). Alignment features on the magazine 54 and drawer 51 allow the operator to orient the magazine 54 properly on the drive mechanism and the thermal control unit when the magazine 54 is loaded onto the rotatable table 52. Once the drawer 51 and magazine 54 are manually inserted into the optical analyzer 16, the drive mechanism rotates the magazine 54 at which time a bar code reader station 58 (FIG. 4A) inventories the samples. A level sensor (not shown) verifies that each optical cup or cuvette 22 contains the correct sample volume. An operator can access the optical analyzer 16 when a user interface indicates that all the samples in the optics cups or cuvettes 22 have been analyzed and drawer 51 is prevented from being opened when any of the components of optical analyzer 16 are moving or when the UV-light sources of the optics system 44 are on.

FIG. 4A illustrates the magazine 54 on rotatable table 52 while being positioned within optical analyzer 16. The optical analyzer 16 further includes a mechanical locking system (not shown) which positions the drawer 51 accurately with respect to the optics system 44. The drive mechanism is configured to automatically rotate the magazine 54 to position each cartridge 12 into the bar code reader station 58 and into precise alignment with the optics system 44. A second mechanical locking system (not shown) is used to secure each optics cup or cuvette 22 in its proper positioning relative to the optics system 44 for optical analysis.

FIG. 4A illustrates the thermal control for the optical cups or cuvettes 22. Preferably, the temperature of each optics cup or cuvette 22 is decreased to a temperature which will slow the metabolism of the bacteria while increasing the fluorescence signal. The thermal control unit 47 which is a thermal electric cooler (TEC) cools a large thermal mass 60 which is located on the rotatable table 52 underneath the magazine 54. The thermal mass 60 (FIG. 4A) is in direct contact with the optical cups or cuvettes 22.

In an alternative embodiment, the invention includes a system for cooling and controlling the temperature of a sample in the optics cup or cuvettes 22 carried by the disposable cartridges; cuvettes or optics cup of the invention. The system of the invention may find particular application in an optical analysis of the specimens in that the fluorescence signal will change with a change of temperature, thus resulting in an inadequate analysis of the specimens.

Figure 13:
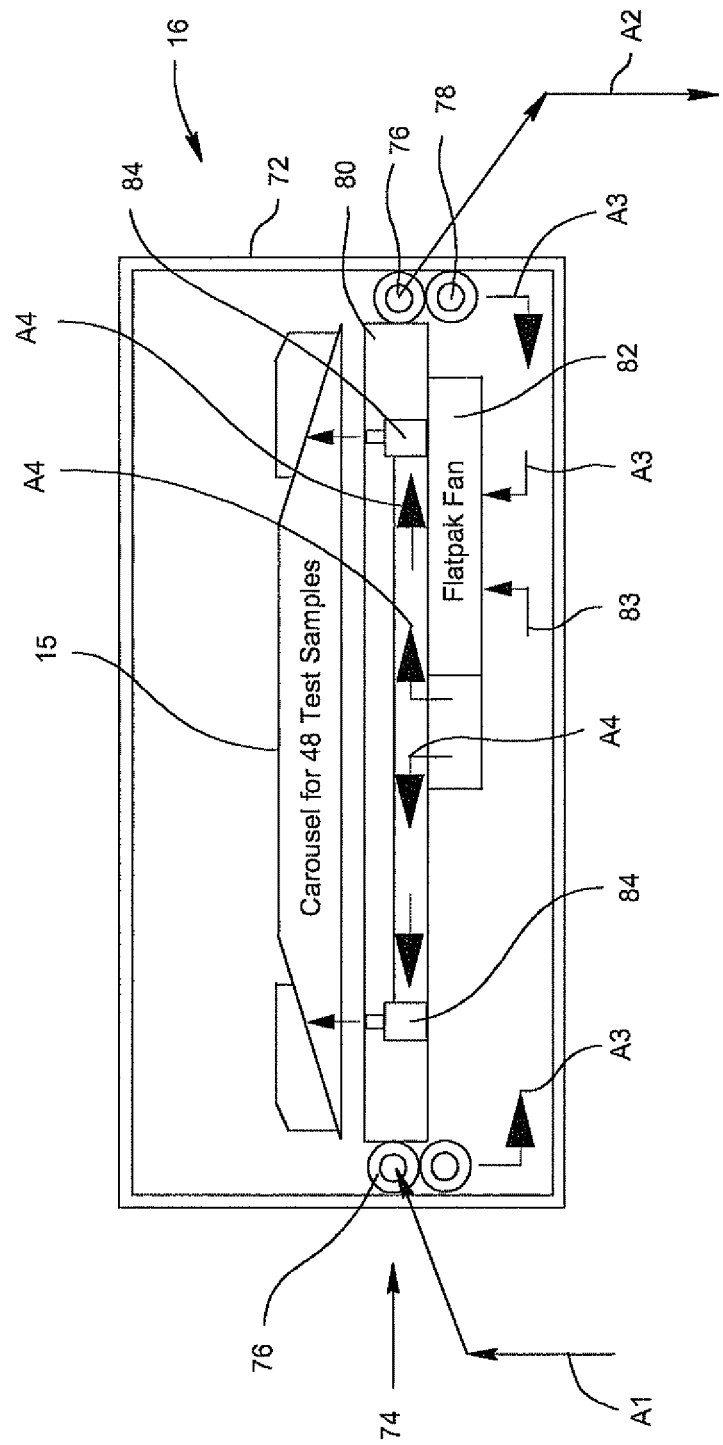
FIG. 13 is a schematic illustrating the pathways for air jets provided in a system of the invention and involves liquid cooling that is converted into air flow cooling.

FIG. 13 illustrates a schematic for a system for delivering water, which cools air, which, in turn, is delivered to cool specimens. More specifically, an optical analyzer 16 includes a housing 72 for enclosing a carousel 15 which supports a plurality of disposable cartridges (not shown), which, in turn, support an optics cup or cuvette (not shown) containing a specimen. A tubing system 74 surrounds the outer periphery of a turntable 80 and includes an upper finned tubing 76 and a lower finned tubing 78, which carry water around the turntable 80. As indicated by arrow A1 located to the left of FIG. 13, chilled water from a thermal electrical (TE) cooler (not shown) is delivered to upper finned tubing 76, and as indicated by the arrow A2, located to the right of FIG. 13, cool water is delivered from upper finned tubing 76 to the TE cooler or chiller at a rate of about 0.5 to 1.0 gallon per minute. The temperature of the chilled water delivered to the upper finned tubing 76 is maintained between ±0.1° C. of a desired temperature for cooling the specimens. This is achieved by detecting the temperature of the cool water being delivered to the TE chiller, indicated by arrow A2, and using this information to adjust the water temperature of the chilled water being delivered from the TE chiller, indicated by arrow A1, to the temperature needed to adequately cool down and maintain the samples at a desired temperature. The several thick, black arrows A3 indicate that the air surrounding the lower finned tubing 78 is drawn upwardly into a Flatpak fan 82 (i.e., a low profile fan) and the several thick, black arrows A4 indicate that the air from Flatpak fan 82 travels into the turntable 80 and upwardly into openings 84 of turntable 80 and through openings of carousel 15 as indicated by arrows A5.

Figure 14:
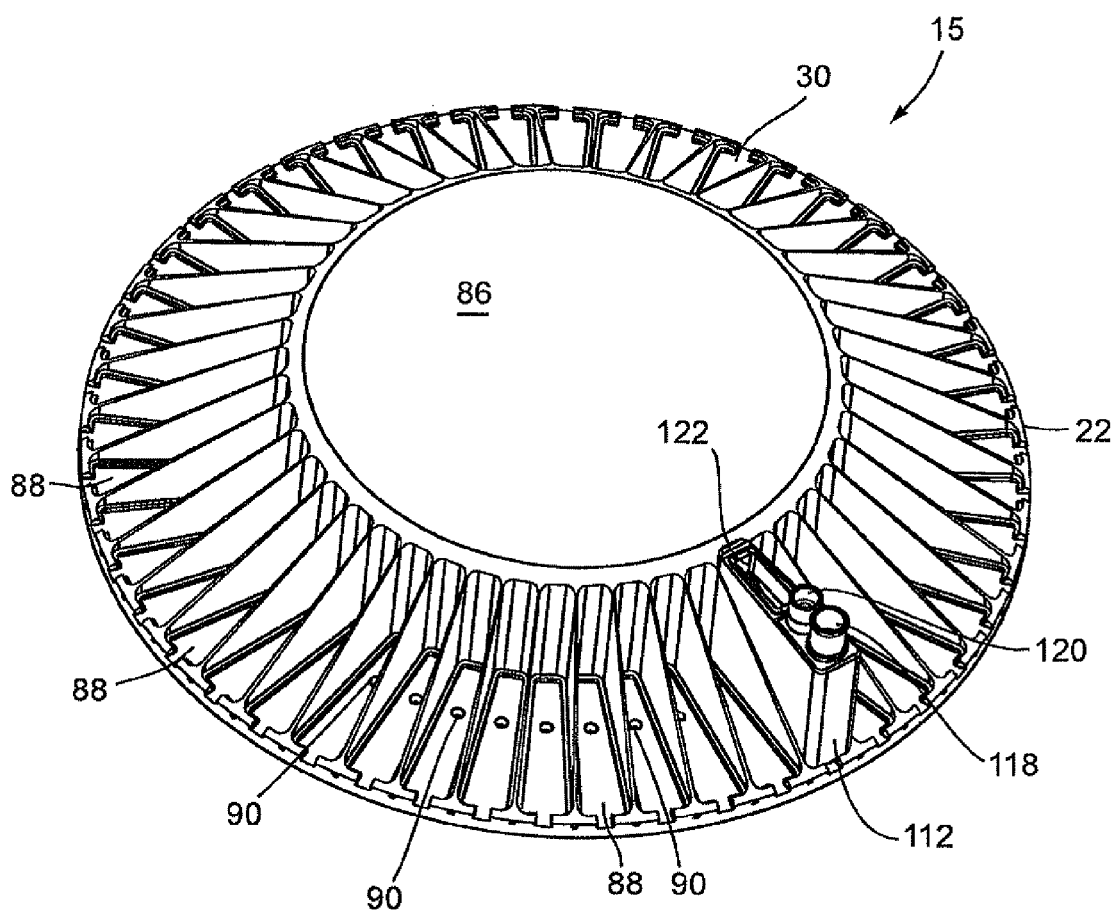
FIG. 14 is a top perspective view illustrating a carousel supporting a disposable cartridge, which in turn, is carrying a disposable optics cup and a plurality of air passageways in the carousel.
Figure 15:
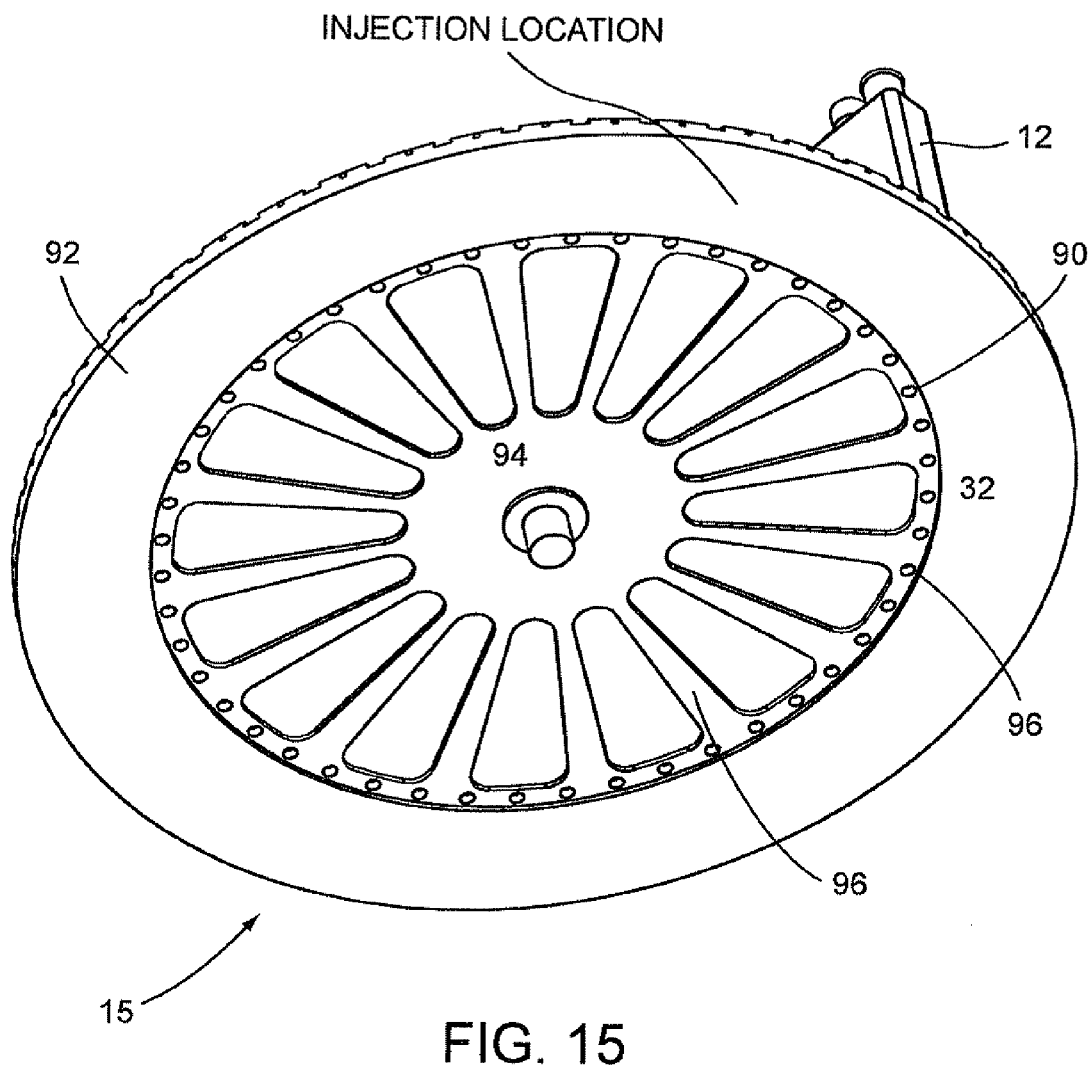
FIG. 15 is a bottom perspective view of the carousel of FIG. 14.

As best shown in FIG. 14, an upper surface 86 of carousel 15 has a plurality of sections, some of which are indicated by reference number 88. Each section 88 forms a cell and has an opening 90. The cool air distributed by Flatpak fan 82 traveling from openings 84 of turntable 80 travels through openings 90 and into its respective cell of sections 88. As best shown in FIG. 15, a lower surface 92 of carousel 15 has an inner hub 94, a number of radial ribs 96 extending from inner hub 94 and an outer ring 98 connected to radial ribs 96 and including the plurality of openings 90 for delivering the cool air into sections 88 mounted to the upper surface 86 of carousel 15. The openings 90 may be 0.156 inch holes. Since the carousel 15 has around 48 compartments or sections 88, and each compartment or section 88 has an opening 90, then the air flow rate of the jets of cool air being delivered through openings 90 and into compartments or sections 88 may range from about 15 to 20 cubic feet per minute.

Referring to FIGS. 14 and 15, it is to be appreciated that each section 88 forming the carousel 15 supports a disposable cartridge 112, similar to the cartridge 112 as in FIGS. 2 and 3A. Each disposable cartridge 112 contains a centrifuge tube 118, a pipette tip 120 and a disposable optics cup or cuvette 122 (FIG. 14) for carrying a specimen. The centrifuge tube 118 and pipette tip 120 are generally used to prepare and process the sample in the disposable optics cup or cuvette 122 for an optical analysis of the contaminants, e.g., organisms in the specimen in the optical analyzer 16 of FIG. 13. Each cartridge is received within a compartment. As can be seen in FIG. 14, each compartment includes a lower recessed lip portion that receives clips 113, 115, and 117. Also, the alignment member 116 is adapted to cooperate with one of the adjacent walls defining the respective compartments that receive the disposable cartridge 112, so that alignment member contacts one compartment wall and the other compartment wall contacts the wall 114 opposite the alignment member 116 for horizontal alignment. Alignment member 116 is optional and is shown in phantom in FIG. 8E.

Preferably, the turntable 80 is made of aluminum and the disposable cartridges 112 and the optics cups or cuvettes 122 are injection molded transparent plastic.

Referring again to FIGS. 13 and 16, in the optical analyzer 16, the carousel 15 made up of the sections 88 is supported by the turntable 80 that locates and positions the optics cups or cuvettes 122 (FIG. 14) one by one, under the optical system (not shown). The cooling system of the invention as described with reference to FIG. 13 is intended to operate to cool the specimen in the optics cup or cuvettes 122 to the desired temperature. For example, each specimen may be cooled from an ambient temperature down to a desired temperature, e.g. around 18° C. within approximately five minutes after start-up of the cooling system of FIG. 13 and then the temperature may be controlled to within ±0.5° C. of the desired temperature until the optical analysis of the samples is completed. Since the turntable 80 is aluminum, the disposable cartridges 112 and optics cups or cuvettes 122 are plastic, and the optics cups or cuvettes 122 are supported in the disposable cartridges 12, which, in turn, are supported in the sections 88 of the carousel 15, convective cooling is used to assist the cool jet airs traveling through openings 90 and into sections 88 in the rapid cooling of the samples.

A further embodiment of the invention envisions a turntable similar to that described and illustrated above with reference to FIGS. 13-15. An aluminum block is located below the turntable and has a plurality of passageways in association with the turntable for carrying chilled air from a TE chiller or cooler to the turntable and cool air from the turntable and, thus, the carousel to the TE chiller for cooling the samples and then cooling the temperature of the specimens in a similar manner described hereinabove with reference to FIGS. 13-15.

The optics system 44 of the optical analyzer 16 will now be described. The optics system is shown in greater detail in FIG. 4B. The optics system 44 contains three separate units, that is, an excitation unit 44($a$), an optical collection unit 44($b$) and a spectrometer. Excitation will be provided by a ultraviolet (UV) light source, which preferably will be LED (light emitting diode). A series of five LED modules provide an excitation unit 44($a$) and will sequentially provide excitation signals to each sample cup or cuvette 22, 122 or 188 at five different excitation wavelengths which will be applied to each sample cup or cuvette 22, 122 or 188 in the same order. The excitation time will be approximately 14 seconds per wavelength. The excitation emissions are directed via lenses and filters 44($d$) to be directed to an upper surface of the sample in the cuvette 22, 122 or 188. In order to narrow or control the shape of each excitation wavelength, narrow bandwidth filters will be used. These filters will direct in a downwardly direction the excitation wavelengths E to the sample cups or cuvettes 22 and the fluorescent emissions F will be reflected back in an upwardly direction to the optical collection unit from the same position of the cassette. The fluorescent emissions can be separated and directed via a filter arrangement. FIG. 4C illustrates the positioning of the optics system 44. As described previously, mechanical locking features position the drive mechanism such that the sample cup or cuvette 22 is aligned precisely. This precise alignment allows for the reflection of the fluorescent emission to the optics system 44 allowing for measurement of fluorescence. Optical elements (not shown) are utilized to gather and direct the fluorescent emissions into the spectrometer for measurement.

In addition, the optical collection unit includes optical elements to gather and direct the fluorescent emissions of the samples in the cups or cuvettes 122 into the spectrometer.

Figure 5:
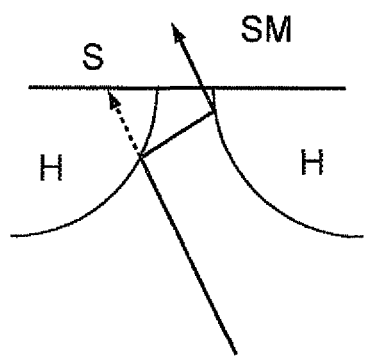
FIG. 5 is a schematic illustrating mirrored convex "horn" that may be provided at the entrance of a slit of a spectrometer.
Figure 6:
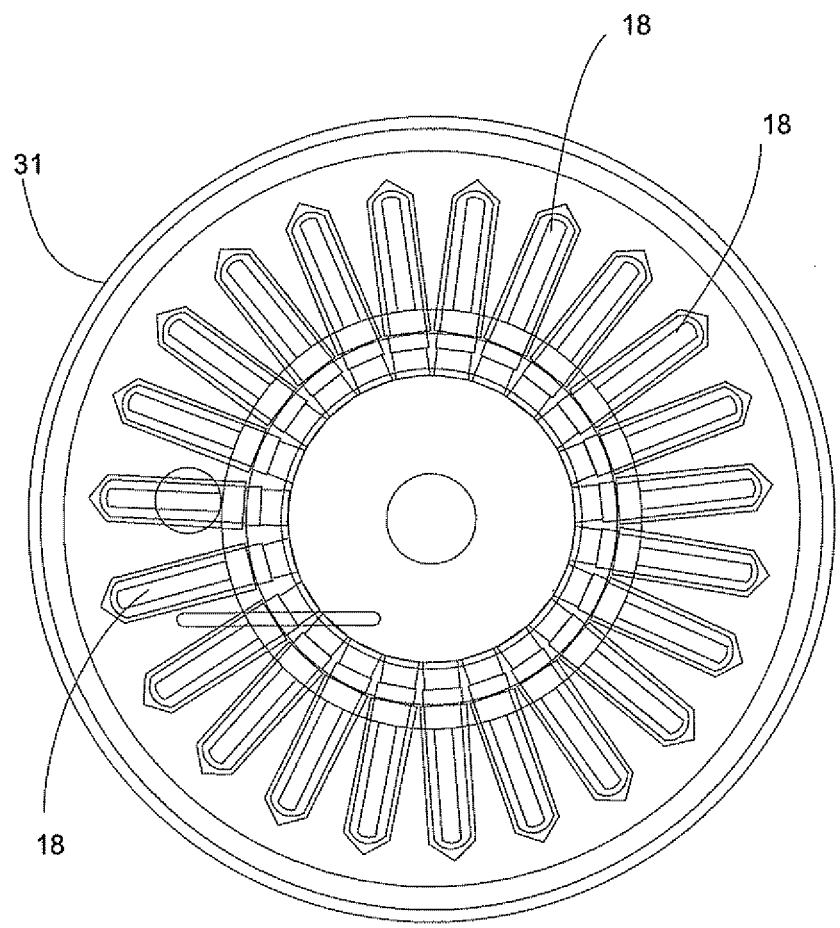
FIG. 6 is a perspective view of a centrifuge illustrating in phantom the several components of the centrifuge of the system of the invention.

The optics system 44 (FIGS. 4B and 4C) may include a Czerny-Turner spectrometer with a CCD (charged couple device) Photon Detector, whereby fluorescent photons are reflected by several mirrors before contacting the CCD device. The emitted fluorescence will be monitored on the CCD device by integrating for a period of time. It is also envisioned that the Czerny-Turner spectrometer be modified with additional cylindrical lenses adjacent the entrance slit and the CCD device in order to improve photon usage efficiency. Additionally, as schematically illustrated in FIG. 5, mirrored convex "horn" H may be provided at the entrance of the slit S of the spectrometer SM to direct additional photons through the slit S.

Referring to FIG. 4A, the optics system 44 will include a light-tight enclosure or housing 64 in order to minimize light entering the optics system 44, and the camera of the CCD device will include a thermal electric cooler (TEC) (not shown) for transferring heat from the camera chip to the enclosure or housing 64 of the optics system 44.

The spectrometer of the optics system will now be described. The arrangement of components for a spectrometer of the invention receives an illumination beam which exits an optical collection system adjacent an optics cup or cuvette used in an optical analyzer which identifies and quantifies the presence of contaminants, e.g., bacteria in specimens.

Figure 16:
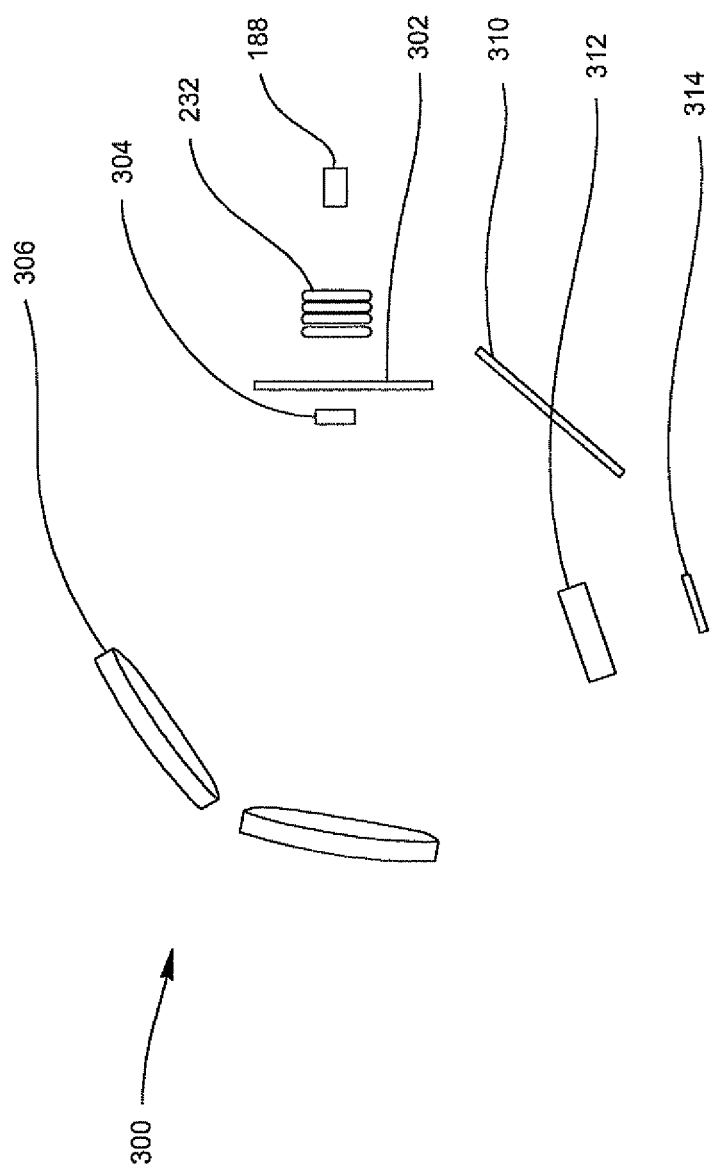
FIG. 16 is a schematic illustration of an arrangement of components for a spectrometer.

Referring first to FIG. 16, a spectrometer 300 of the invention is used in conjunction with an optical collection unit 232 having a plurality of lenses and an optics cup or cuvette 188 containing a urine specimen. The spectrometer 300 includes a spectrometer slit 302 located immediately adjacent to the optical collection unit 232 and a first cylinder lens 304 located immediately adjacent to the slit 302 in the same path of travel for an illumination beam as that of the optical collection unit 232 and optics cup or cuvette 188. A first collimating mirror 306 and a second collimating mirror 308 are located to the far left of the first cylinder lens 304, and a grating 310 is located to the bottom of optical collection unit 232. A second cylinder lens 312 and a CCD sensor 314 are located to the left of the grating 310 in FIG. 16.

The illumination beam enters optics cup or cuvette 188 from a light source (not shown) in a manner discussed above and fluorescent light is emitted out of optics cup or cuvette 188 and through the lenses of the optical collection unit 232. From optical collection unit 232, the fluorescence beam travels through the spectrometer slit 302 and through the first cylinder lens 304. From first cylinder lens 304, the fluorescence beam travels along a first optical path and toward the first light collimating mirror 306. The beam is reflected from collimating mirror 306 and travels upon a second optical path through grating 310. The fluorescence beam in grating 310 is dispersed into a plurality of dispersed beams which are reflected off of grating 310 and travel along a third optical path toward the second collimating mirror 308. These dispersed beams strike the second collimating mirror 308 which, in turn, focuses the dispersed beams toward and through the second cylinder lens 312 along a fourth optical path. From the second cylinder lens 312, the dispersed beams are then received in the CCD sensor 314. The spectral information is captured by the CCD sensor 314 for the optical analysis of the urine specimen in optics cup or cuvette 188.

The first mirror 306, the second mirror 308 and the grating 310, are preferably spherical in shape and have a 3-inch diameter. The grating 310 preferably is a plane diffraction grating having 1200 lines per millimeter (lpm) and blazed 10.4° for a 300 nm wavelength region. Such an appropriate grating is manufactured by and obtained from the Newport Corporation under product Model No. 53-030R.

Figure 17:
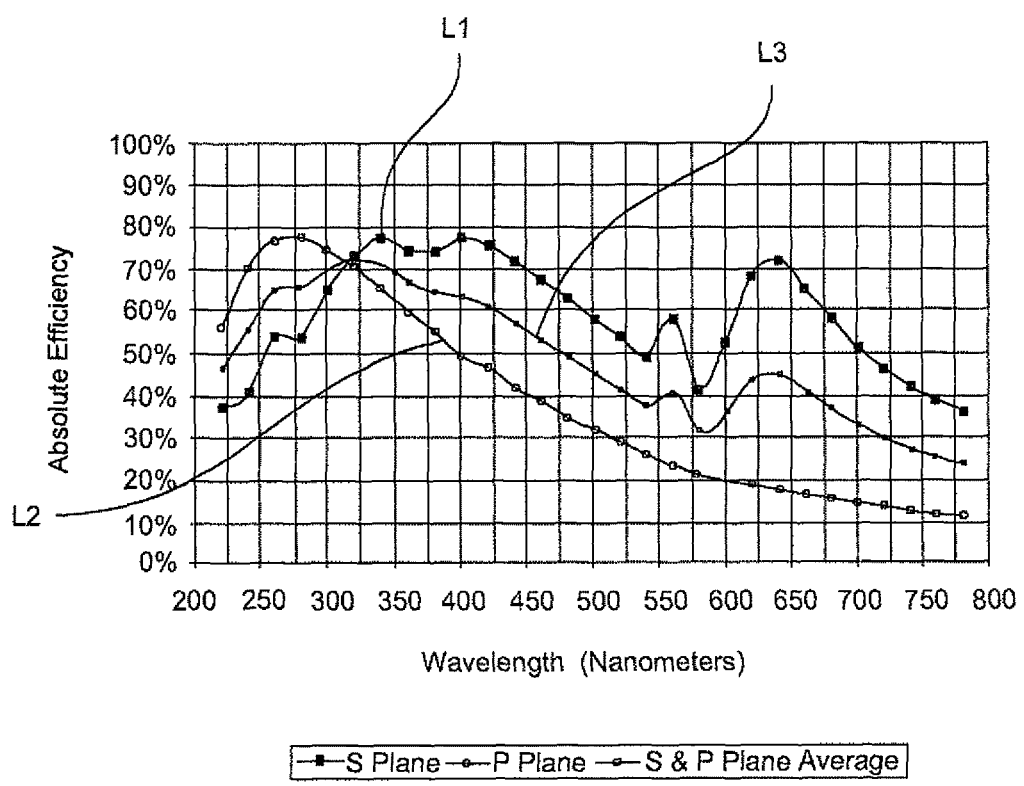
FIG. 17 is a graph illustration of the response of a grating used in the arrangement of FIG. 16 plotting the absorbance efficiency versus the wavelength of the illumination beam.

A grating response for this type of grating 310 is illustrated in FIG. 17, wherein line L1 represents the S-Plane, line L2 represents the P-Plane and line L3 represents the average of the S-Plane and the P-Plane. As can be appreciated from the graph of FIG. 21, the best absorbent efficiency occurs in the 300 to 400 nm wavelength region, which is the region of interest for the grating necessary in the spectrometer 300 of the invention.

Referring again to FIG. 16, the first cylindrical lens 304 and the second cylindrical lens 312 are made of fused silica and are components referred to as components off the shelf or COTS. The first cylindrical lens 304 located adjacent spectrometer slit 302 is located approximately 10.7 mm from slit 302 and is a CVI Model No. CLCX-15.00-10.2-UV, and the second cylindrical lens 312 located adjacent to CCD sensor 314 is a CVI Model No. RCX-400 25.4-15.3-UV.

Still referring to FIG. 16, the first collimating mirror 306 adjacent the spectrometer slit 302 has a nominal radius of about 400 m and the second collimating mirror 308 has a nominal radius of about 350 m. The ratio of the focal lengths of first collimating mirror 306 and second collimating mirror 308 is adjusted in order to fit the 300 to 420 nm spectrum of the illumination beam into the chip of the CCD sensor 314.

The CCD sensor 314 may be a Hamamatsu Model No. S7031-1008 chip which is approximately 25 mm wide and 6 mm long. The CCD sensor 314 preferably is a single-stage cooled unit which uses thermal electrical cooling (TEC). For a bandwidth range of 300-400 nm, which is the wavelength range of interest for the present invention, the quantum efficiency of the chip for the preferred CCD sensor 314 is approximately 50%.

Still referring to FIG. 16, the dimensions for the slit of the spectrometer slit 302 is nominally 2.8 mm wide and 5 mm long. Using a source bandwidth of 10 nm FWHM and a triangular function for the source output with wavelength, the spectral width of the system of FIG. 16 at the plane of the CCD sensor 314 is 12.5 nm FWHM. The acceptance angle of the spectrometer 300 of FIG. 16 is approximately 0.4 NA (nano-Angstroms).

Figure 20:
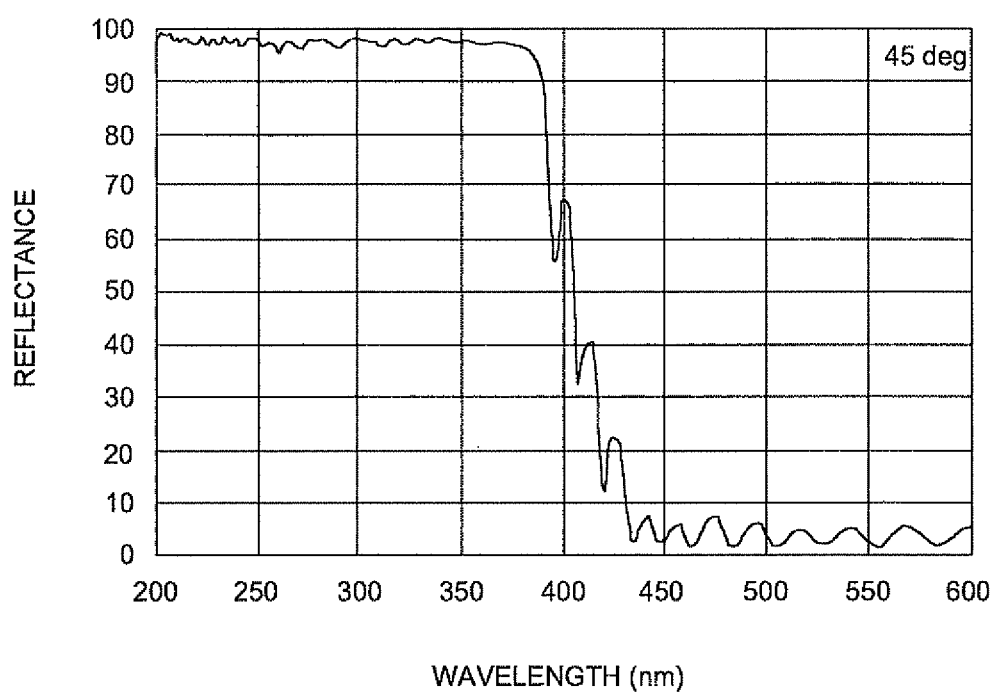
FIG. 20 is a graph illustrating reflectance versus wavelength of the turning mirror within the illumination arrangement of FIG. 18.

In the arrangement 300 of the invention, the first cylindrical lens 304 tends to capture the additional radiation of the fluorescence beam exiting the spectrometer slit 302 and then direct the radiation through the optics system of FIG. 16. The second cylindrical lens 312 in close proximity to the plane of the CCD sensor 314 tends to focus this radiation onto the pixels in the CCD plane which are about 6 mm in length. It is the inventor's position that the combination of the first cylindrical lens 304 and the second cylindrical lens 312 enhances the throughput of the spectrometer 300 of FIG. 20 compared to conventional spectrometers which do not include lenses similar to lenses 304 and 312 of the invention.

The spectrometer 300 of FIG. 16 may generally be similar to a Crossed-Czerny-Turner layout with the addition particularly of the first cylindrical lens 304 and the second cylindrical lens 312 to create a low resolution (less than 10 nm) but highly sensitive spectrometer for use with wavelengths in the 300 nm to 420 nm range. The plane of the CCD sensor 314 represents a 25 mm length detector.

The sample processor 14 will have a HEPA air-filtering system for ventilation purposes in filtering the air exiting the sample processor 14.

It is further envisioned that the LED intensity will be monitored to correlate the emitted fluorescence with the intensity of the excitation fluorescence. In particular, the information obtained by the optical analyzer 16 may be used to generate graphs similar to FIGS. 5 through 9 of U.S. Publication No. 2007/0037135 A1, which is commonly owned and herein incorporated by reference in its entirety, described in greater detail below. The graphs represent for the concentration of the bacteria in the sample cups or cuvettes 22, the fluorescence intensity, the emission wavelengths and the excitation wavelengths.

An illumination arrangement for exciting and optically collecting light in the optics cup or cuvette 122 used in an optical analyzer 16 which identifies and quantifies the contaminants in the sample is shown in FIGS. 18-21 and is discussed in more detail below.

A known measuring system is shown in U.S. Pat. No. 7,277,175 B2 which discloses a system and method for wavelength selective measurement of properties of liquid samples. More specifically, the system includes a light source, an optical delivery system, at least two optical systems, a sample holding assembly, a filter assembly, a transmission system and a detector. The filter assembly may be a group of filters contained in a filter wheel. This system may provide for measuring properties of small volume liquid samples that allows the insertion of selective wavelength filters in an optical train in the vicinity of the measurement location in order to increase the signal-to-noise ratio. However, this system does not provide for a compact optical reader having an increased signal-to-noise ratio for optically analyzing the bacteria in a urine specimen.

Figure 18:
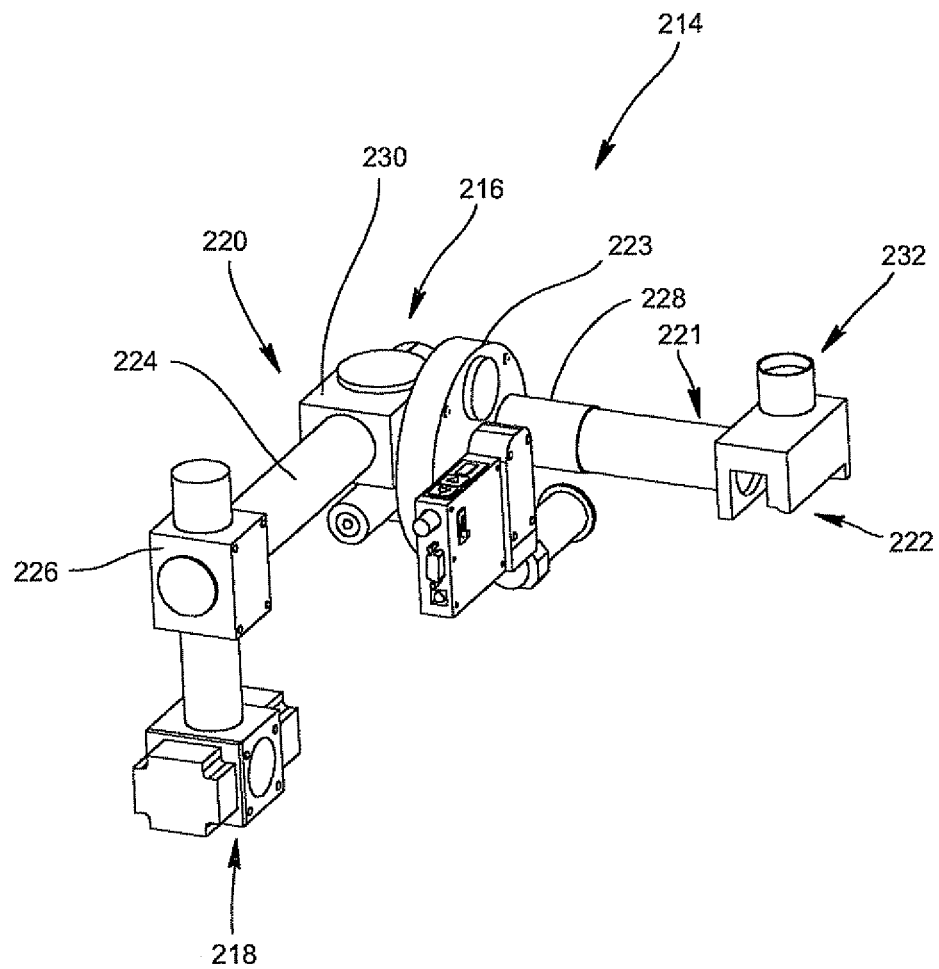
FIG. 18 is a perspective view illustrating an illumination arrangement of the optical reader of the invention.
Figure 21:
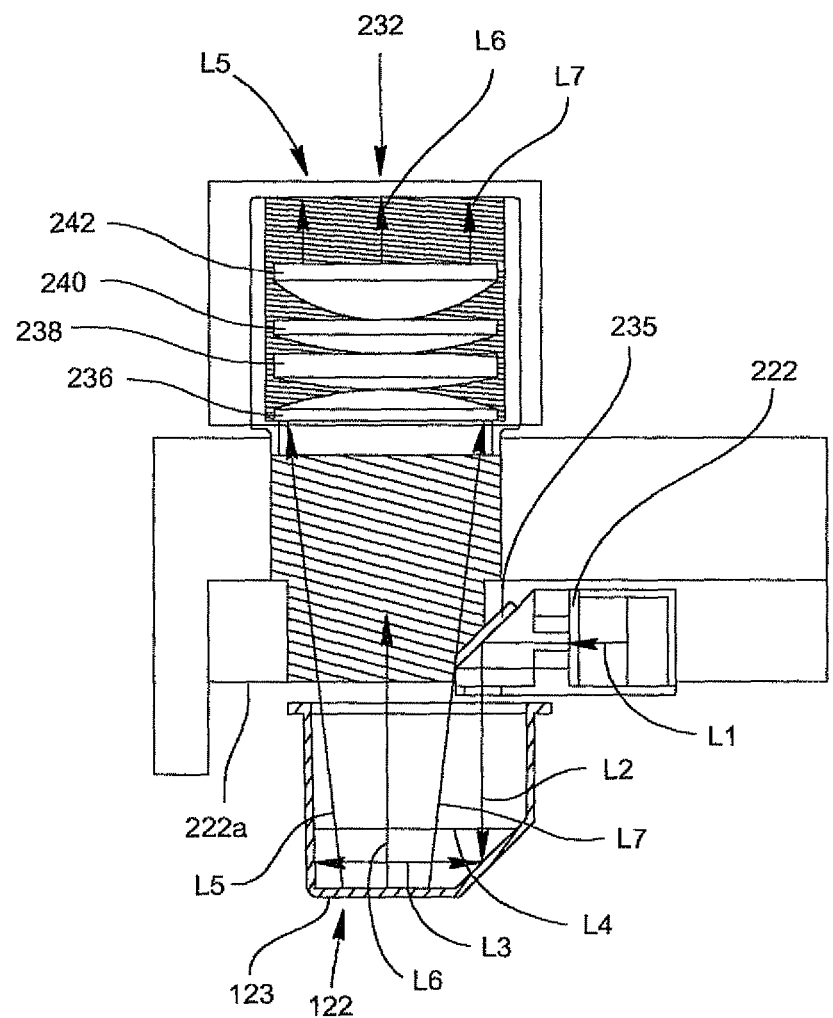
FIG. 21 is a schematic illustrating an optics cup positioned in the illumination arrangement of FIG. 18.

The present invention provides an improved optics system including an optical reader that has a compact carriage train arrangement which produces and directs collimated light into a specimen for an optical analysis, while providing an increased signal-to-noise ratio for an improved analysis of the specimen. Referring first to FIG. 18, an optical reader 214 of the invention includes an illumination arrangement 216, a light source 218 for producing an illumination beam, a first optical system 220, a second optical system 221, an anchor shoe 222 and a filter wheel 223 located between the second optical system 221 and the anchor shoe 222. The light source 218 may be Xenon, LED's, deuterium and others. Even though a filter wheel 223 is shown in FIG. 18, a linear varying filter may be used. The first optical system 220 includes a carriage 224 having a housing 226 for supporting a turning mirror and a filter (not shown). The second optical system 221 includes a carriage 228 having a housing 230 for supporting a turning mirror and a filter (not shown). As shown in FIG. 18, the carriage 224 of the first optical system 220 extends into the housing 230 of the second optical system 221 to connect the first optical system 220 to the second optical system 221. The carriage 228 of the second optical system 221 extends into the filter wheel 223 and into the housing 230 of the second optical system 221 and into the anchor shoe 222 to connect the second optical system 221 to the anchor shoe 222. The anchor shoe 222 includes a turning mirror (not shown) located to the right of a slot 222a, as shown in FIG. 21, for receiving an optics cup or cuvette containing a fluid sample and an optical collection device 232 located above the slot 222a which contains a plurality of lenses (more about which is discussed herein below).

As is generally known to those skilled in the art, a filter is used to transmit light only in particular regions of the spectral and is used to change or modify the total or relative energy distribution of a beam of light. A turning mirror is at various location points to change the direction that the light is traveling. A lens is used for focusing or non-focusing light thereby allowing different optical effects. A slit is generally an opening having a specific shape. The light that passes through the slit travels to a grating and into a device, such as a CCD camera for detection.

The illumination arrangement 216 of FIG. 18 further includes a filter wheel 223. As disclosed in column 4, lines 10-23 of the above-mentioned U.S. Pat. No. 7,277,175 B2, a filter wheel contains a group of filters, wherein a pre-selected filter may be placed in an optical path of collimated electromagnetic radiation. The pre-selected filter substantially selects transmission in a predetermined wavelength region. The filters generally are pre-selected based on the desired sample to be measured and the width of the spectrum of the absorption (or emission) band arising from the interaction of electromagnetic radiation and the sample. For a biological sample, electromagnetic radiation absorption is centered at wavelengths ($\lambda$) ranging from 200 nm to 800 nm, mostly at 230 nm, 260 nm and 280 nm.

The lenses used in the optical collection device 232 may be commercial off-the-shelf (COTS) components.

Figure 19:
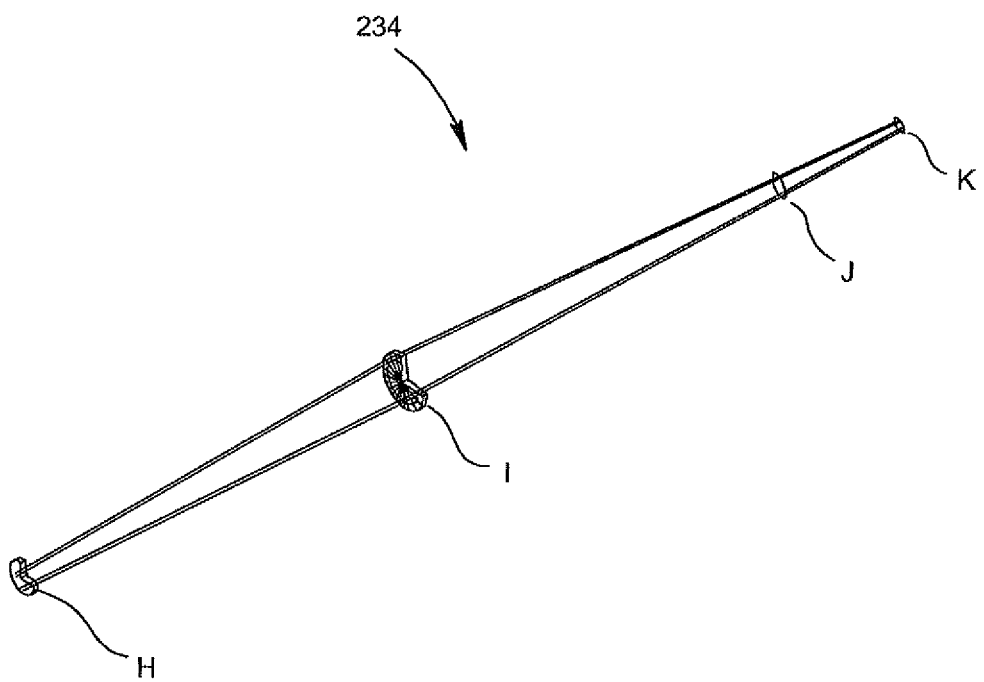
FIG. 19 is an illustration showing the path of travel of the light beam from the light source to the specimen produced by the illumination arrangement of FIG. 18.

FIG. 19 illustrates a typical illumination beam indicated at reference numeral 234 showing a theoretical simulation of the beam path from a light source to a specimen produced by present day lens arrangements. In FIG. 23, a lamp or light source (not shown) is located to the left of a first lens system H, I, J and K, and a second lens system is approximately 8 inches away from the first lens system with the output at an illumination shoe aperture (not shown) in the system which is located to the far right in FIG. 19. In the invention, the length of this illumination beam 234 of FIG. 19 is reduced by the illumination arrangement 216 of FIG. 18 wherein the illumination arrangement 216 incorporates the filter wheel 223. Filter wheel 223 may carry a plurality of narrow band filters, i.e. in the ultraviolet range. In this instance, the radiation from light source 218 of FIG. 18 may be restricted to wavelengths ranging from 260 nm to 300 nm. Alternatively, filter wheel 223 may carry filters that provide the whole light spectrum and associated wavelengths. Also, as discussed herein above, a linear varying filter may also be used instead of the filter wheel 223. The turning mirrors (not shown) in the first optical system 220 and the second optical system 221 of the illumination arrangement 216 of FIG. 18 are custom filters which predominantly reflect the ultraviolet band.

FIG. 18 illustrates a graph of custom filters which are Newport thin films provided by Newport Corporation, which are used as turning mirrors in the first optical system 220 and the second optical system 221 of the illumination arrangement 216 of FIG. 18. As illustrated, these custom filters produce a relatively high reflectance that is about 100, in the ultraviolet range that is in wavelengths ranging between 200 nm and 380 nm and a low reflectance, i.e., 68 to lower than 10 in the visible light (VIS) and irradiation (IR) ranges, i.e., from about 400 nm to 608 nm. Thus, the filters may be VIS, NIR, and/or FIR rejecting filters.

The optical cup or cuvette 22 PCT Application US2008/079533, also discussed in detail above and used in the cartridge 12 of FIGS. 1A, 1B, and 2 has an elongated cylindrical body and a lower tapered end. In this design, the ultraviolet (UV) light source in the optical analyzer is directed down the middle of the cuvette and into this lower tapered end for the optical analysis of the biological specimen. The optical cup or cuvette 122 shown in FIGS. 12A-12C, 13, 14A-14C and cup or cuvette 188 shown in FIG. 15, is designed to optimize the fluorescence sensing of the transmitted light rays in the cup or cuvette 122, 188.

FIG. 21 is a schematic of a side view of the anchor or injection shoe 222 and optical collection device 232 of the illumination arrangement 216 of FIG. 18, wherein an optics cup or cuvette 122, as discussed above, is positioned within the slot 222a of anchor shoe 222.

Referring back to FIGS. 9A, 9B, 10, and 21, an example of the optics cup or cuvette 122 is shown, which may be used in the optical reader of the invention. Optics cup or cuvette 122 includes a rectangular-shaped container 123 having a lower tapered area 124 and an inner reflective surface. The container 123 further includes two parallel spaced-apart sidewalls 160, 162, two spaced-apart end walls 164, 166, and a horizontal floor 168, and wherein the first end wall 164 includes the tapered area 124 which is contiguous to the horizontal floor 168. The width of the horizontal floor 168 of the optics cup or cuvette 122 is about 7 mm, the depth of the sidewalls 160, 162 and the second end wall 166 is about 18 mm, the depth of the first end wall 164 is about 11 mm, the length of the horizontal floor 168 is about 16 mm and the length of the tapered area 124 is about 7 mm. The tapered area 124 is angled at about a 45° angle relative to the first end wall 164.

Still referring to FIG. 21, the inner surface of optics cup or cuvette 122 is reflective and preferably made of aluminum with a high quality surface finish or having a micro-roughness less than 50 angstroms. The optics cup or cuvette 122 may be made of a low leaching and fluorescence signal material, for example, plastic or glass. Optics cup or cuvette 122 may be an injection molded plastic, which may subsequently be subjected to a metallization step using evaporated aluminum. This approach will allow a low cost mechanical fabrication with a batch process coating. A further approach for manufacturing optics cup or cuvette 122 for use in the invention is to use an aluminum foil liner ribbon 174, as shown in FIG. 9A along the inner surface length of the container 123 which forms to the shape of the first end wall 164, the lower tapered area 124, the floor 168 and the second end wall 166 as discussed above. The volume of the liquid specimen contained in the optics cup or cuvette 122 may be approximately 955 µl.

Referring again to FIG. 21, a line L1 represents the incoming illumination beam. This illumination beam is produced by the illumination arrangement 216 of FIG. 22 and passes through a slit (not shown) which nearly collimates the illumination beam. The slit is approximately a 4×4 mm square in cross-section and is located in the anchor shoe 222. The illumination beam is reflected into the optics cup or cuvette 122 using a turning mirror 235 located in the anchor shoe 222 as discussed herein above. The first surface that a beam L2 encounters is the 45° inner surface of lower tapered area 124 of optics cup or cuvette 122. A reflected beam L3 traverses the optics cup or cuvette 122 in the volume of liquid represented by a line L4. Upon striking the reflective inner surface of the second end wall 166, the beam returns to the reflective inner surface of the 45° lower tapered area 124, fluorescence is emitted upwardly and out of optics cup or cuvette 122 and toward the anchor shoe 222. The expansion of the beam is controlled by the optics system of the optical reader 214 (FIG. 18) of the invention and generally may be about 5×5 mm in cross-section upon its return to the anchor shoe 222.

It is to be appreciated that in view of the optics cup or cuvette 122, the beam in optics cup or cuvette 122 is directed such that it does not illuminate the bottom or floor 168 of the optics cup or cuvette 122 during its traversal in the liquid volume of the specimen. Optical collection device 232 located above the slot 222a contains a plurality of lenses indicated at 236, 238, 240, and 242 and views the floor 168 of the optics cup or cuvette 122 and the liquid in the optics cup or cuvette 122 as indicated by lines L5, L6 and L7 which is representative of the emitted fluorescent rays in FIG. 21. Approximately 47% of the liquid volume of the specimen is read by the optical fluorescent collection device 232. By eliminating the illumination of the floor 168 of optics cup or cuvette 122 and by restricting the optical collection device 232 to view only the floor 168 and not the sidewalls 160, 162 and end walls 164, 166 of optics cup or cuvette 122 (FIGS. 9A and 9B), the background fluorescence of the optics cup or cuvette 122 as seen by the optical collection device 232 can be minimized or nearly eliminated. Raytrace modeling indicates that a factor of 1000× less noise could be theoretically attainable. This is a huge advantage to achieving higher signal-to-noise ratios. By eliminating the noise of fluorescence from the optics cup or cuvette 122, the signal is more prominent, and higher fidelity and sensitivity can be achieved. Transmission of the illumination beam and measurement of the emitted fluorescence may occur in concert per sample or the illumination into the sample may stop during the measurement of the fluorescence.

The following equation details the SNR (signal-to-noise ratio) calculation:

$$SNR = \frac{S}{\sqrt{S + B_f}} + B_r$$

S represents the signal. $B_f$ represents background fluorescence and $B_r$ represents Raman background which occurs in view of the liquid water in the specimen. For optical readers of the prior art, the signal-to-noise ratio (SNR) is approximately 8.1 with over 1.5e6 noise photons from fluorescence and 1e4 photons from the signal. In the design of the present invention, the noise is expected to be reduced to 1.5e4 noise photons, while the signal is expected to increase to about 1.2e4 photons. In view of these results, it is anticipated that the SNR produced by the present invention will be about 73.

As discussed hereinabove, the optical analyzer 16 provides results that are then used to identify the type of bacteria in the urine samples. This can be done by coupling the optical analyzer 16 to a computer module (not shown) and feeding in the acquired information of the optical analyzer 16, such as the fluorescence emission, into the computer module. The computer module may perform multivariate analysis on the fluorescence excitation-emission matrices of the urine samples to identify and quantify the urine samples in a manner similar to that disclosed in the above U.S. Publication No. US 2007/0037135 A1. Here, the system includes a fluorescence excitation module which includes an excitation light source, a sample interface module for positioning the sample to receive the light source, a fluorescence emission module and a detection device. The computer module described above is coupled to the fluorescence module. The multivariate analysis may comprise extended partial least squared analysis for identification and quantification of the urine samples.

It is still further envisioned that a "homogenitor tube" will be used to mix the different LED packages output into a uniform UV light source. A typical "homogenitor tube" for use in the invention will be similar to that known to those skilled in the art.

It will be understood by one of skill in the art that the fluid sample may be for example a biological, chemical or toxicant sample, e.g., urine sample which is optically analyzed, for example, for the type and amount of organism or microorganism, e.g., bacteria in the sample.

The present invention has been described with reference to the preferred embodiments. Obvious modifications and alterations will occur to others upon reading and understanding the preceding detailed description. It is intended that the invention be construed as including all such modifications and alterations.

The invention claimed is:

1. An optics cup for holding a biological sample for use in an optical analysis comprising:
   a rectangular-shaped container made of a transparent material and containing the biological sample, said container including two spaced-apart sidewalls, a first end wall, a second end wall, and a floor;

said container having a rectangular opening for receiving the biological sample and a lower tapered area extending from said first end wall and inwardly and downwardly relative to the rectangular opening and toward said floor and wherein the first end wall has a depth that is less than a depth of said sidewalls and said second end wall, and wherein the lower tapered area has a surface that is configured to receive an illumination beam fed through the opening and to reflect the beam through the biological sample.

2. An optics cup as claimed in claim 1, further comprising a wet ribbon liner for light collection through the biological sample for the optical analysis of the biological sample.

3. An optics cup according to claim 2, wherein the wet ribbon liner is made of a reflective material which is shaped and formed to partially clad the inside of the container including the lower tapered area.

4. An optics cup according to claim 2, wherein the wet ribbon liner is made of a reflective material which is shaped and formed to substantially clad the inside of the container including the lower tapered area.

5. An optics cup according to claim 2, wherein the wet ribbon liner is fastened to a flange of the rectangular opening of the container through a crimping process.

6. An optics cup according to claim 2, wherein the wet ribbon liner is secured to the flange of the rectangular opening of the container by at least a one-way retention tab.

7. An optics cup according to claim 2, wherein the ribbon liner is secured to the flange of the rectangular opening of the container by at least a heat staked pin.

8. An optics cup according to claim 2, wherein the container further includes a snap mechanism and wherein the wet ribbon liner is secured to the container by the snap mechanism.

9. An optics cup according to claim 1, wherein the cup is an injection molded cup and made of a leaching resistance material for minimizing the amount of contaminants leached out of the biological sample.

10. An optics cup according to claim 1, wherein the opening of the container is configured to receive the illumination beam therethrough and the tapered area is positioned at a location to receive the illumination beam and for reflecting the illumination beam through the biological sample and into contact with the second end wall and back toward the tapered surface resulting in upwardly emittance of fluorescence out of the container for optical analysis.

11. An optics cup for holding a biological sample for use in an optical analysis comprising:

a rectangular-shaped container made of a transparent material and containing the biological sample, said container including two spaced-apart sidewalls, a first end wall, a second end wall, and a floor;

said container having a rectangular opening for receiving the biological sample and a lower tapered area extending from said first end wall and inwardly and downwardly relative to the rectangular opening and toward said floor and wherein the first end wall has a depth that is less than a depth of said sidewalls and said second end wall, and wherein the tapered area has a surface that is configured to receive an illumination beam fed through the opening and to reflect the beam through the biological sample, and wherein an inner surface at least along the tapered area is coated with a layer of reflective material.

12. An optics cup according to claim 11, wherein the layer of reflective material is aluminum and is coated to the inner surface of the container through a process selected from the group consisting of a vacuum metallization process and an electroplating process.

13. An optics cup according to claim 11, wherein the layer of reflective material extends partially along the inner surface of the container including the lower tapered area.

14. An optics cup according to claim 11, wherein the layer of reflective material extends substantially along the inner surface of the container including the lower tapered area.

15. An optics cup for holding a biological sample for use in an optical analysis comprising:

a two-piece construction having an upper piece with an upper rectangular opening and a lower rectangular opening for receiving the biological sample and a lower piece including a lower tapered area for holding the biological sample, said lower piece including two spaced-apart sidewalls, a first end wall comprising the lower tapered area, a second end wall, and a horizontal floor wherein the lower tapered area extends inwardly and downwardly relative to the upper rectangular opening toward and contiguous with the horizontal floor, and wherein the lower tapered area has a surface that is configured to receive an illumination beam fed through the openings and to reflect the beam through the biological sample.

16. An optics cup according to claim 15, wherein the upper piece and the lower piece are bonded together and wherein the lower piece contains a layer of reflective material.

17. An optics cup according to claim 15, wherein the upper piece and the lower piece are bonded together through a bonding process selected from the group consisting of an ultrasonic butt welding process, an ultrasonic shear welding process, a press fit process, a snap fit process and a solvent weld process using a press fit or snap fit process.

18. A disposable sample cup for containing a biological specimen for optical analysis of the bacteria in the biological specimen, comprising:

a rectangular-shaped container having a tapered area, a rectangular-shaped top opening for receiving the biological specimen, and an inner reflective surface, said container further including two parallel spaced-apart sidewalls, two spaced apart end walls and a horizontal floor, and said two spaced-apart end walls including a first end wall and a second end wall and wherein the first end wall has the tapered area extending therefrom and contiguous to the horizontal floor, wherein the first end wall has a depth that is less than a depth of said sidewalls and the second end wall, and wherein the tapered area has a surface that is configured to receive an illumination beam fed through the opening and to reflect the beam through the biological sample.

19. A disposable sample cup according to claim 18, wherein said tapered area is a straight wall.

20. A disposable sample cup according to claim 19 wherein said straight wall has an angle of approximately 45° relative to one of the spaced apart end walls.

21. A disposable sample cup according to claim 18, wherein the inner reflective surface is selected from the group consisting of a narrow aluminum ribbon and an aluminum coating and wherein the inner reflective surface is arranged along the first end wall, the tapered area, the horizontal floor and the second end wall of the container.

22. A disposable sample cup according to claim 18, wherein the container is made of transparent material selected from the group consisting of plastic and glass.

23. A disposable sample cup according to claim 18, wherein the container further includes a flange along the perimeter of the rectangular-shaped opening for supporting the sample cup during analysis of the biological specimen.

24. A disposable cartridge for use in the identification and quantification of micro-organisms in biological samples, comprising:
   a plurality of compartments for positioning and supporting a plurality of disposable components including a centrifuge tube, a pipette and an optics cup containing the processed biological sample for use in an optical analysis;
   the optics cup having a rectangular shape and a tapered area into which a light source travels for the optical analysis of the processed biological sample and a reflective surface for enhancing the optical analysis, said optics cup including two spaced-apart sidewalls, a first end wall, a second end wall, said first end wall having a depth that is less than a depth of the sidewalls and the second end wall, and wherein the tapered area extends from the first end wall, wherein the tapered area has a surface that is configured to receive an illumination beam fed through an opening of the optics cup and to reflect the beam through the biological sample; and
   the compartment for positioning and supporting the optics cup having a rectangular-shaped opening for receiving and supporting the rectangular-shaped optics cup.

25. The disposable cartridge according to claim 24, wherein the disposable cartridge is injection molded and made of a plastic material.

26. The disposable cartridge of claim 24, wherein the compartments for positioning and supporting the centrifuge tube and the pipette are cylindrically shaped and extend substantially the length of the centrifuge tube and the pipette.

27. The disposable cartridge according to claim 24, wherein the compartment for positioning and supporting the optics cup is substantially enclosed within the disposable cartridge and has a configuration similar to that of the optics cup.

28. The disposable cartridge according to claim 24, including at least one attachment clip configured for cooperating with a magazine opening for attaching the cartridge therein.

29. The disposable cartridge according to claim 28 including at least one alignment member.

30. An optics cup for holding a biological sample for use in an optical analysis comprising:
   a rectangular-shaped container made of a transparent material and containing the biological sample, said container including two spaced-apart sidewalls, a first end wall, a second end wall, and a floor;
   said container having a rectangular opening for receiving the biological sample and a lower tapered area extending from said first end wall and inwardly and downwardly relative to the rectangular opening and toward said floor, and wherein the first end wall has a depth that is less than a depth of said sidewalls, and wherein the opening of the container is configured to receive an illumination beam therethrough and the tapered area is positioned at a location to receive the illumination beam and for reflecting the illumination beam through the biological sample and into contact with the second end wall and back toward the tapered surface resulting in upwardly emittance of fluorescence out of the container for optical analysis,
   said second end wall and an inner surface at least along the tapered area coated with a layer of reflective material.

31. An optics cup for holding a biological sample for use in an optical analysis comprising:
   a two-piece construction having an upper piece with an upper rectangular opening and a lower rectangular opening for receiving the biological sample and a lower piece including a lower tapered area for holding the biological sample, said lower piece including an upper rectangular opening, two spaced-apart sidewalls, a first end wall comprising the lower tapered area, a second end wall, and a horizontal floor, wherein the lower tapered area extends inwardly and downwardly relative to the upper rectangular opening toward and contiguous with the horizontal floor, wherein the upper and lower openings of the upper piece and the upper opening of the lower piece are configured to receive an illumination beam therethrough and the tapered area is positioned at a location to receive the illumination beam and for reflecting the illumination beam through the biological sample and into contact with the second end wall and back toward the tapered surface resulting in upwardly emittance of fluorescence out of the container for optical analysis.

32. A disposable cartridge for use in the identification and quantification of micro-organisms in biological samples comprising:
   a plurality of compartments for positioning and supporting a plurality of disposable components including a centrifuge tube, a pipette and an optics cup containing the processed biological sample for use in an optical analysis;
   the optics cup having a rectangular shape, an opening, and a tapered area into which a light source travels for the optical analysis of the processed biological sample and a reflective surface for enhancing the optical analysis, said optics cup including two spaced-apart sidewalls, a first end wall, a second end wall, said first end wall having a depth that is less than a depth of the sidewalls and the second end wall, and wherein the tapered area extends from the first end wall, wherein the opening of the optics cup is configured to receive an illumination beam therethrough and the tapered area is positioned at a location to receive the illumination beam and for reflecting the illumination beam through the biological sample and into contact with the second end wall and back toward the tapered surface resulting in upwardly emittance of fluorescence out of the optics cup for optical analysis; and
   the compartment for positioning and supporting the optics cup having a rectangular-shaped opening for receiving and supporting the rectangular-shaped optics cup.

* * * * *

UNITED STATES PATENT AND TRADEMARK OFFICE
CERTIFICATE OF CORRECTION

| | |
|---|---|
| PATENT NO. | : 8,519,358 B2 |
| APPLICATION NO. | : 12/865186 |
| DATED | : August 27, 2013 |
| INVENTOR(S) | : Gal Ingber |

Page 1 of 1

It is certified that error appears in the above-identified patent and that said Letters Patent is hereby corrected as shown below:

In the Claims

Column 27, Line 64, Claim 11, after "wherein" delete "and"

Signed and Sealed this
Twenty-second Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,519,358 B2                                                              Page 1 of 1
APPLICATION NO.  : 12/865186
DATED            : August 27, 2013
INVENTOR(S)      : Ingber et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 238 days.

Signed and Sealed this
Fifteenth Day of September, 2015

Michelle K. Lee
*Director of the United States Patent and Trademark Office*